(12) United States Patent
Parazynski et al.

(10) Patent No.: US 11,014,141 B1
(45) Date of Patent: May 25, 2021

(54) NEEDLE BENDING ASSEMBLY

(71) Applicants: Scott Edward Parazynski, Houston, TX (US); John Spiegel Michels, Jr., Dallas, TX (US); Jeffrey William Bull, Naperville, IL (US); Roy Melling, Borrego Springs, CA (US)

(72) Inventors: Scott Edward Parazynski, Houston, TX (US); John Spiegel Michels, Jr., Dallas, TX (US); Jeffrey William Bull, Naperville, IL (US); Roy Melling, Borrego Springs, CA (US)

( * ) Notice: Subject to any disclaimer, the term of this patent is extended or adjusted under 35 U.S.C. 154(b) by 0 days.

(21) Appl. No.: 17/037,568

(22) Filed: Sep. 29, 2020

(51) Int. Cl.
*B21F 1/00* (2006.01)
*A61B 17/34* (2006.01)
*A61B 17/00* (2006.01)

(52) U.S. Cl.
CPC .......... *B21F 1/002* (2013.01); *A61B 17/3401* (2013.01); *A61B 2017/00526* (2013.01); *A61B 2017/3454* (2013.01)

(58) Field of Classification Search
CPC ............... A61B 17/34; A61B 17/3401; A61B 17/06066; A61B 2017/0608; B21F 1/002; B21F 1/004; B21F 1/00; B21G 1/00; B21G 1/003; B21G 1/006; B21G 1/02; B21G 1/06; B21G 1/08; B21G 1/04; A61M 2207/00; A61M 2005/1581
See application file for complete search history.

(56) References Cited

U.S. PATENT DOCUMENTS 5,201,210 A * 4/1993 Stein, III ................ A61M 5/32
140/123

* cited by examiner

*Primary Examiner* — Diane D Yabut
*Assistant Examiner* — Majid Jamialahmadi
(74) *Attorney, Agent, or Firm* — Steven H Greenfield; Greenfield Invention and Patent Consulting, Inc.

(57) ABSTRACT

Embodiments of assemblies used for bending spinal needles and method for producing bent spinal needles used in medical procedures are disclosed. In one embodiment, a straight needle is placed in position for a fulcrum to apply pressure onto a designated spot on the needle and apply a bending pressure to bend the needle while the needle is supported at both ends. A barrier wall is configured to limit the movement of the needle resulting from the bending force to prevent overbending of the needle. In two other embodiments, a dual angle bending member enables selecting the bending angle desired by the user to be applied onto the needle. The angle of the bent needle is considerably reduced due to metal relaxation; however, the angle reduction is predictable and is taken into account in calculating the target bending angle.

18 Claims, 23 Drawing Sheets

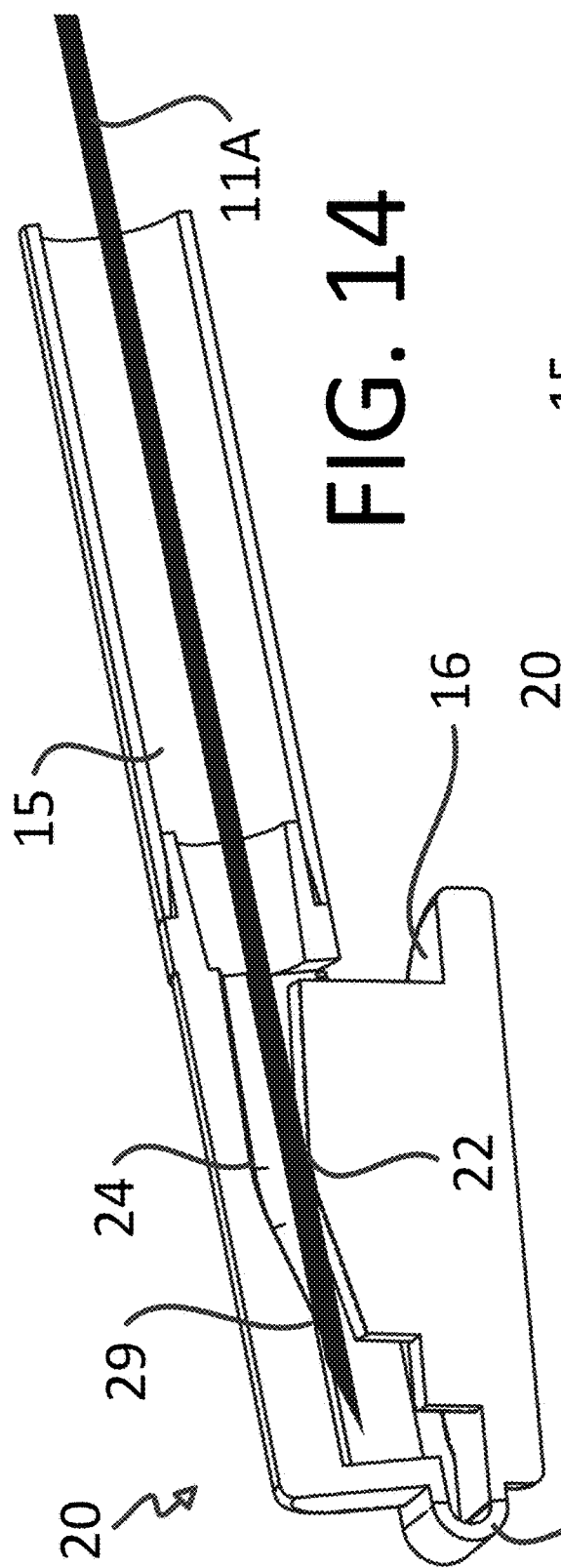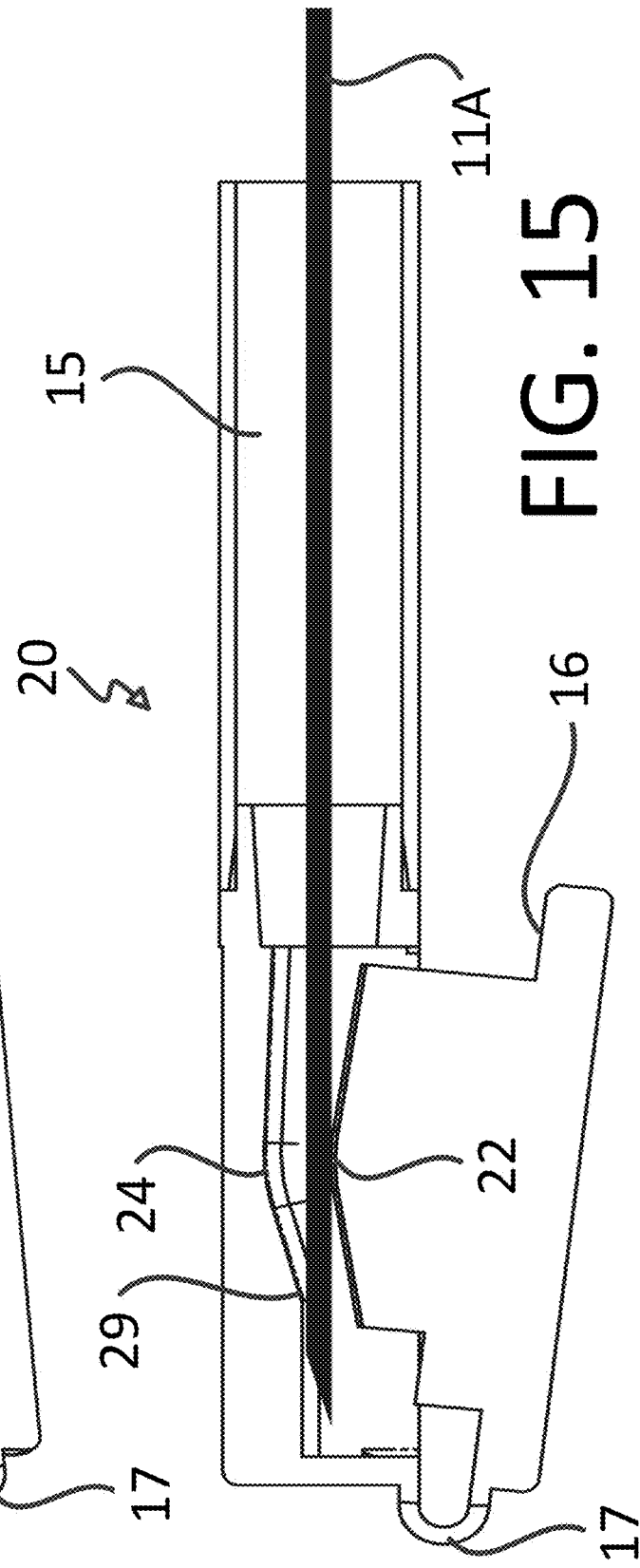

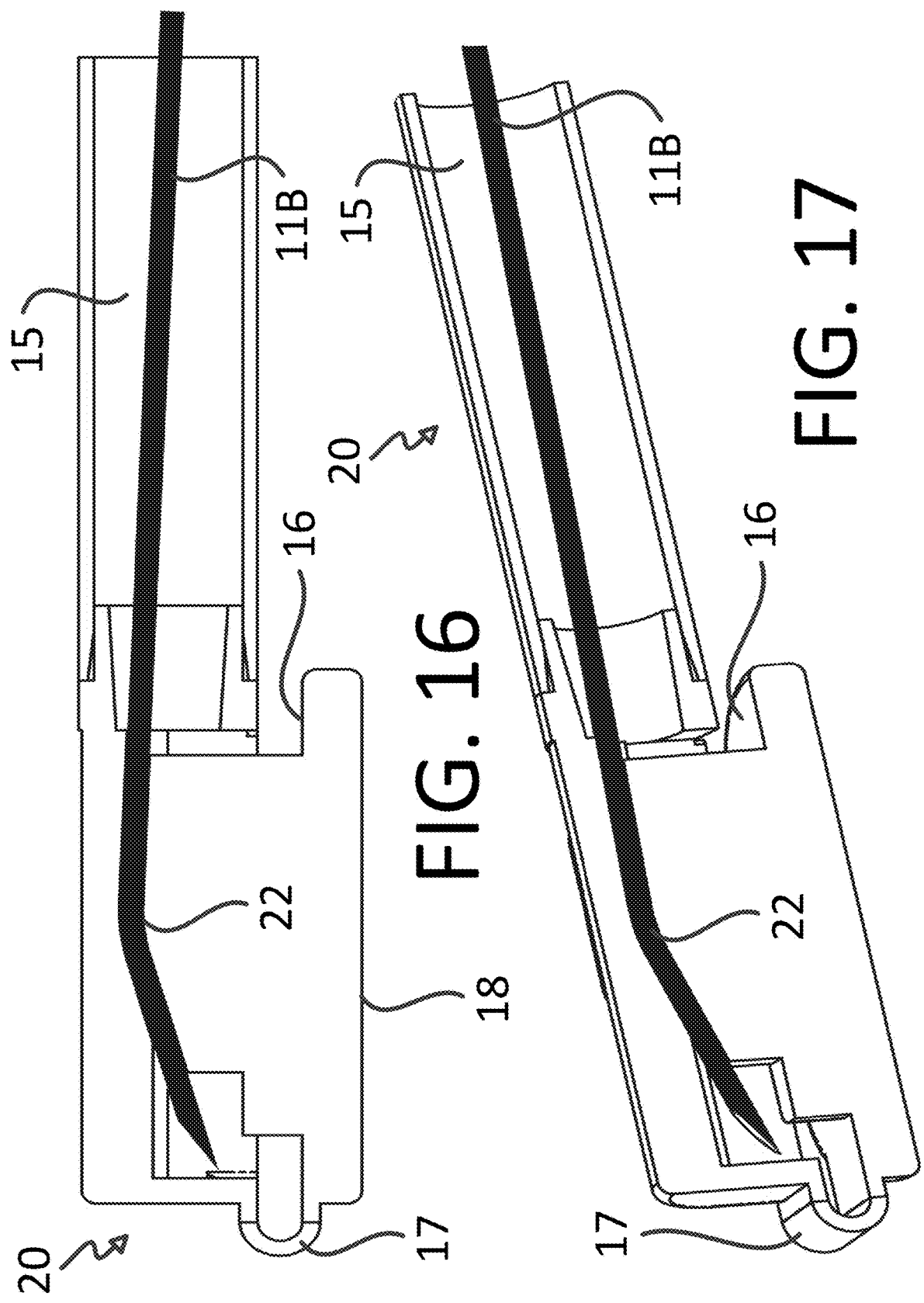

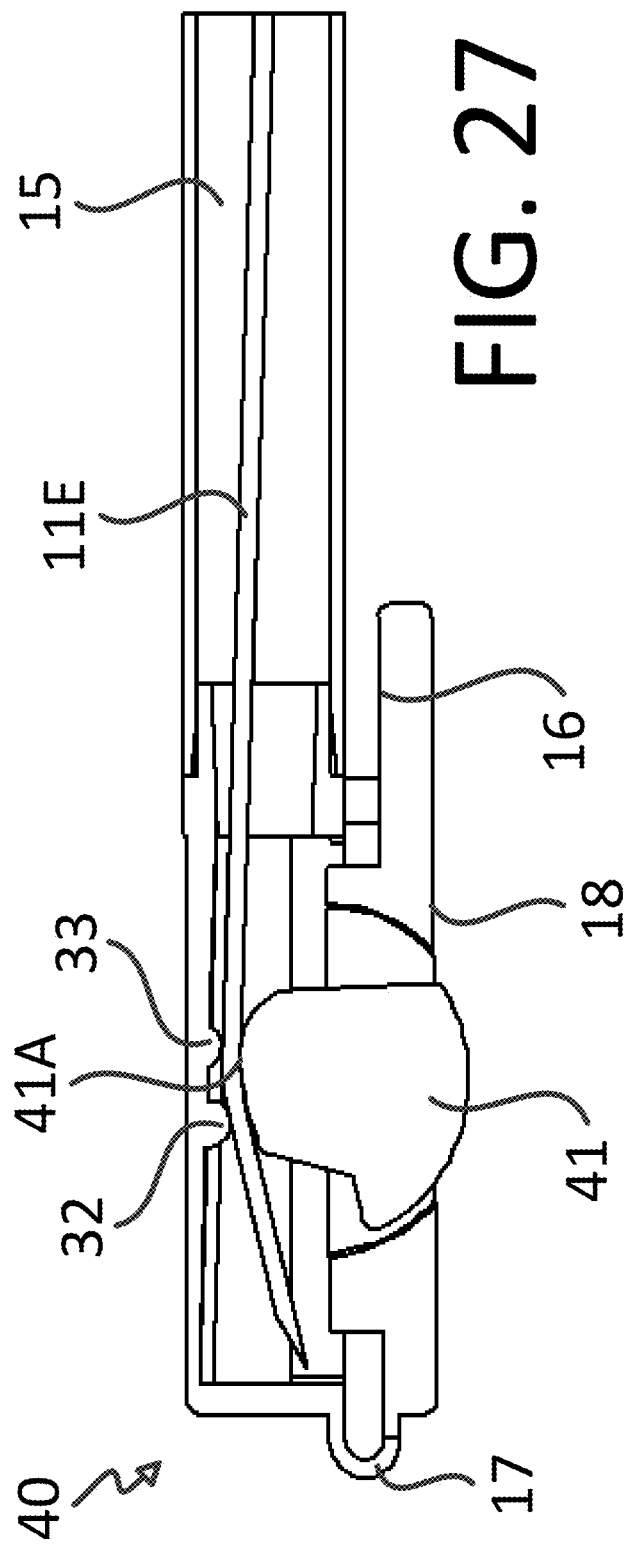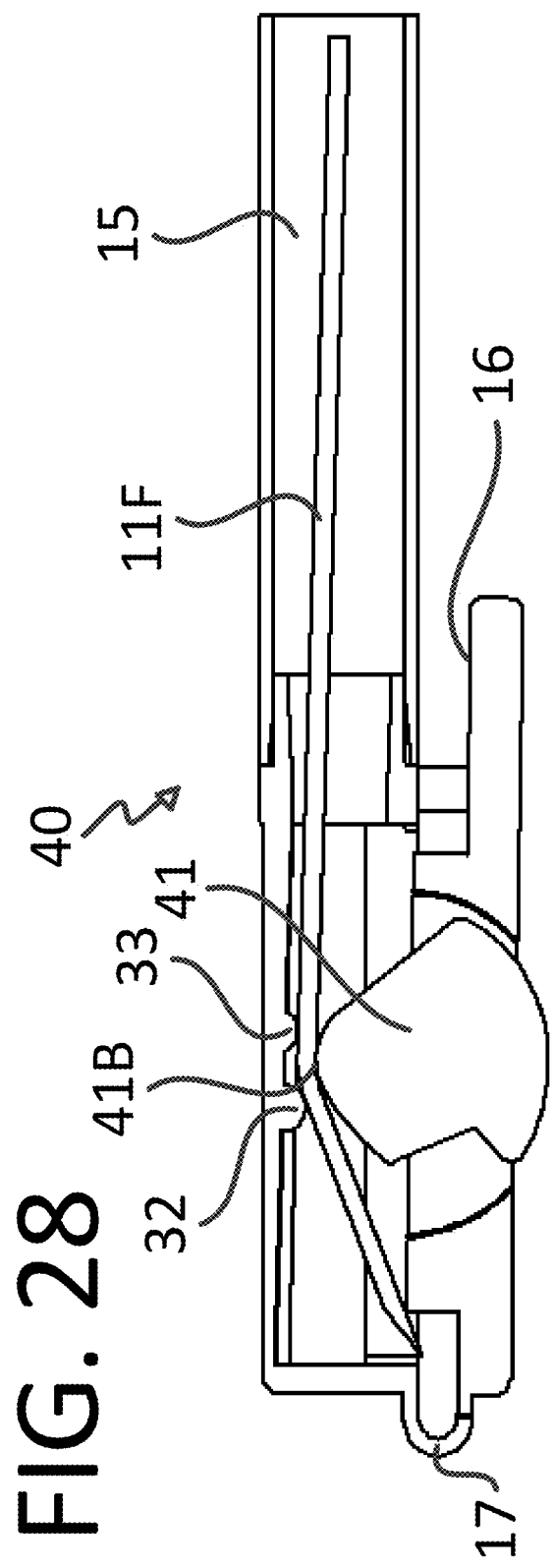

NEEDLE BENDING ASSEMBLY

FIELD OF THE INVENTION

The present invention generally relates to an assembly and to a method for bending needles. More specifically, the present invention relates to an assembly and method for bending spinal needles that are specially constructed needles containing an indwelling metal stylet. These needles are inserted into the spine as well as other body tissues at a predetermined angle to facilitate steering the tip to a desired target, typically aided by intermittent fluoroscopic guidance. The indwelling metal stylet or wire fills the internal diameter of the spinal needle during insertion in the body, preventing tissue or fluid blockage. Once the tip of the needle is at its intended position, the stylet is removed and an anesthetic, steroid or contrast agent may be injected, or spinal fluid removed, as is done for lumbar puncture.

BACKGROUND OF THE INVENTION

Certain therapeutic and diagnostic medical procedures involve the use of long spinal needles that are pre-bent near their tip to facilitate steering towards an intended target. These procedures, typically done using radiologic guidance, e.g., intermittent fluoroscopy, often require maneuvering around skeletal and other vital structures to get to their intended target. In typical practice, a physician would use a needle driver, a type of a surgical instrument intended to grip a surgical needle, to pinch the end of a spinal needle and then introduce a subtle bend in the tip, approximately 5 degrees in magnitude.

Alternatively, physicians will sometimes also bend their needles using just their gloved hands, risking loss of sterilization of the needle due to inadvertent puncture of their glove as well as risk a needlestick injury.

The issues with manually bending a needle tip include: a) the inexact and non-reproducible nature of these bends; b) the "off-axis" nature of the bend, as bending may unintentionally take place in two axes given the way the needle driver must grasp the needle tip; c) risk of unintentional needlestick injury to the physician while manipulating the needle during the bending process; d) risk of damage to the needle itself, especially the critical cutting surfaces of the needle bevel or tip; e) the cost of additional surgical tools, cleaning and sterilization cycles for each and every procedure; and f) the lost time for the physician and support staff. Furthermore, the forces required to bend a needle containing a stylet may exceed those achievable by using finger pressure alone.

Of note, a clinician may purchase especially pre-bent needles, but these are substantially more expensive, and they do not give the option for a straight needle tip in the same packaging.

SUMMARY OF THE PRESENT INVENTION

In one aspect of the present invention, a needle bending assembly comprises a housing containing a needle having a hollow core, the housing and needle having a proximal end and a distal end, the distal end of the needle being supported by a base containing the distal end of the needle, the proximal end of the needle being supported by an upper wall portion of the housing, the proximal end of the housing having a bottom opening; and a bending member configured to fit in the bottom opening and to support the proximal end of the needle, said bending member having a shape of an angle containing a fulcrum configured for applying pressure onto a designated spot of the needle between the proximal end and distal end of the needle, said pressure resulting in bending the needle to a shape of the angle of the bending member.

In another aspect of the present invention, a needle bending assembly comprises a housing containing a needle having a hollow core, the housing and needle having a proximal end and a distal end, the distal end of the needle being supported by a base containing the distal end of the needle, the proximal end of the needle being supported by an upper wall portion of the housing, the proximal end of the housing having a bottom opening; and a dual angle bending member configured to fit in the bottom opening and to support a bottom of the proximal end of the needle, the dual angle bending member having a top surface containing a first section contoured in a shape of a first angle, the first section containing a first fulcrum and a second section contoured in a shape of a second angle, the second section containing a second fulcrum, the dual angle bending member being configured for selecting the first section or the second section for applying bending pressure by the respective fulcrum onto a designated spot of the needle between the proximal end and distal end of the needle, the pressure resulting in overlaying a shape of a selected surface of the dual angle bending member onto the needle.

These and other features, aspects and advantages of the present invention will become better understood with reference to the following drawings, description and claims.

BRIEF DESCRIPTION OF THE DRAWINGS

FIG. 14 is a perspective cross sectional view of the bending assembly showing the needle in a ready to use configuration according to the first embodiment of the present invention;

FIG. 15 is a side cross sectional side view of the bending assembly showing the needle in a ready to use configuration according to the first embodiment of the present invention;

FIG. 16 depicts a cross sectional side view of the bending assembly showing the bent needle in an after-use configuration according to the first embodiment of the present invention;

FIG. 17 illustrates a perspective cross sectional side view of the bending assembly showing the bent needle in an after-use configuration according to the first embodiment of the present invention;

FIG. 27 is a cross sectional side view of the bending assembly showing the bent needle in a first after-use configuration according to the third embodiment of the present invention; and FIG. 28 shows a cross sectional side view of the bending assembly showing the bent needle in a second after-use configuration according to the third embodiment of the present invention;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention. The intended use of the needle bending assembly is in a pre-packaged, sterilized form that contains a straight needle placed in the proper position for bending. To achieve the desired needle shape, the user need only press onto the assembly until movement is stopped.

Figure 1:
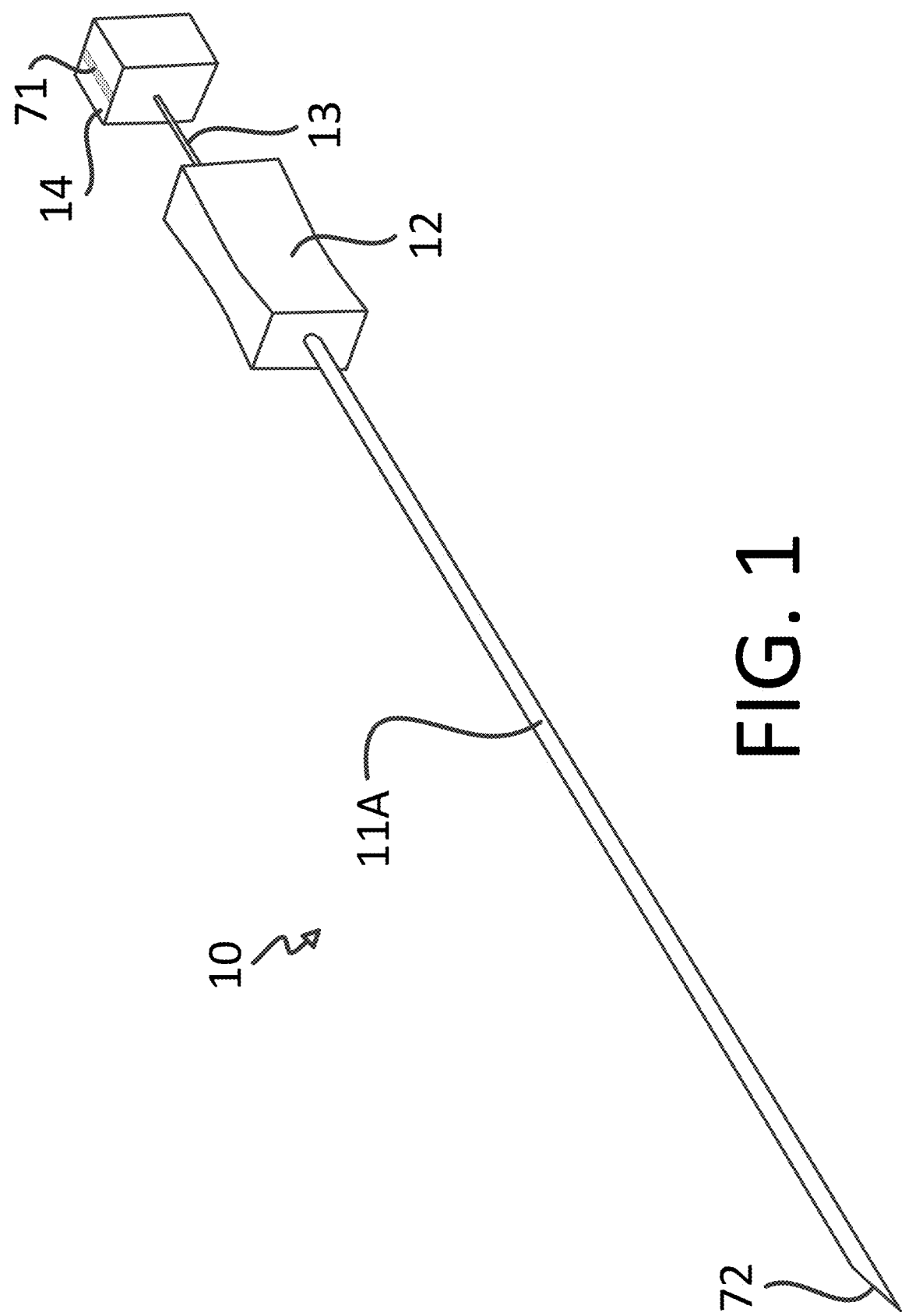
FIG. 1 presents a perspective view of a needle assembly.
Figure 2:
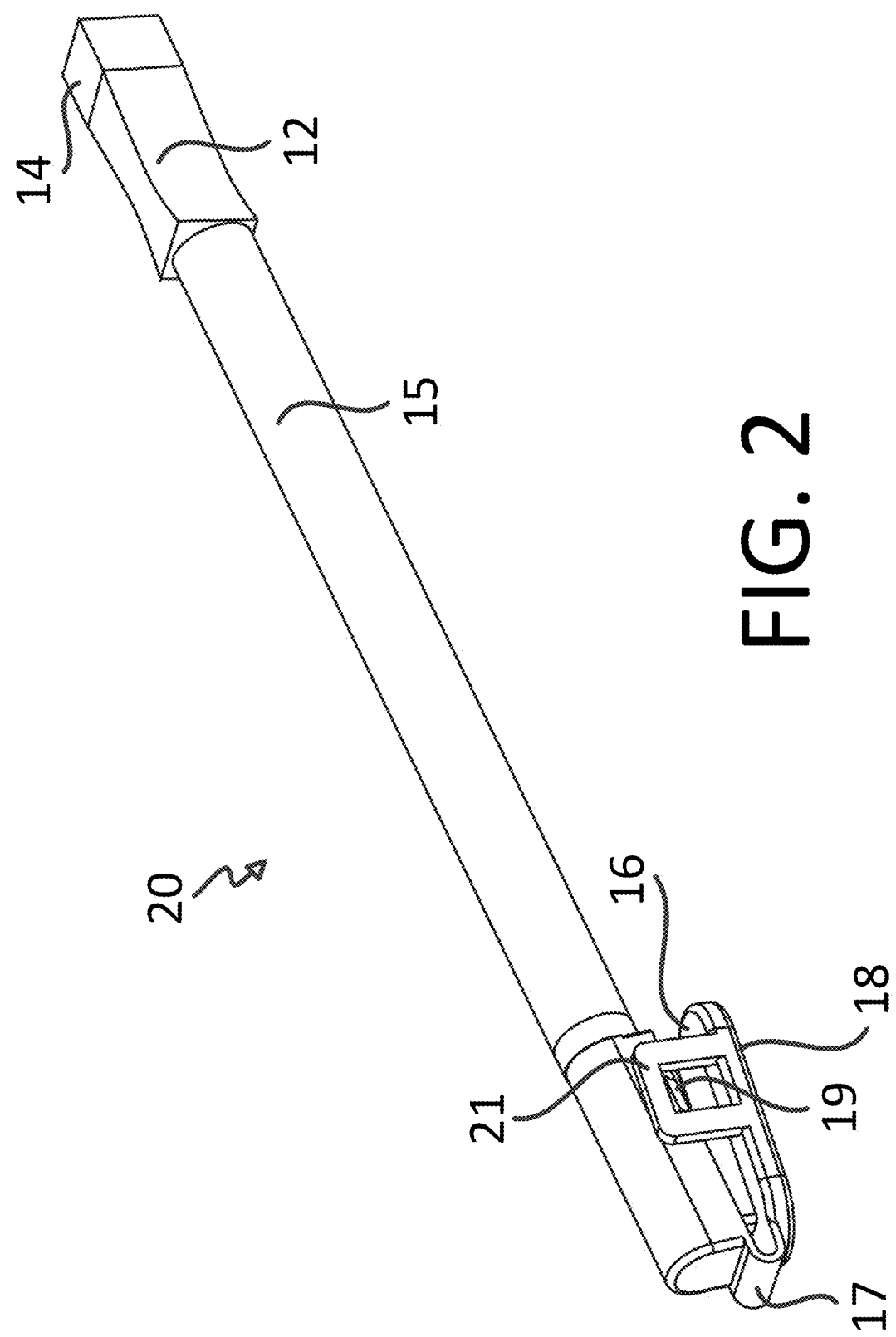
FIG. 2 shows a perspective view of a bending assembly according to the first embodiment of the present invention.
Figure 3:
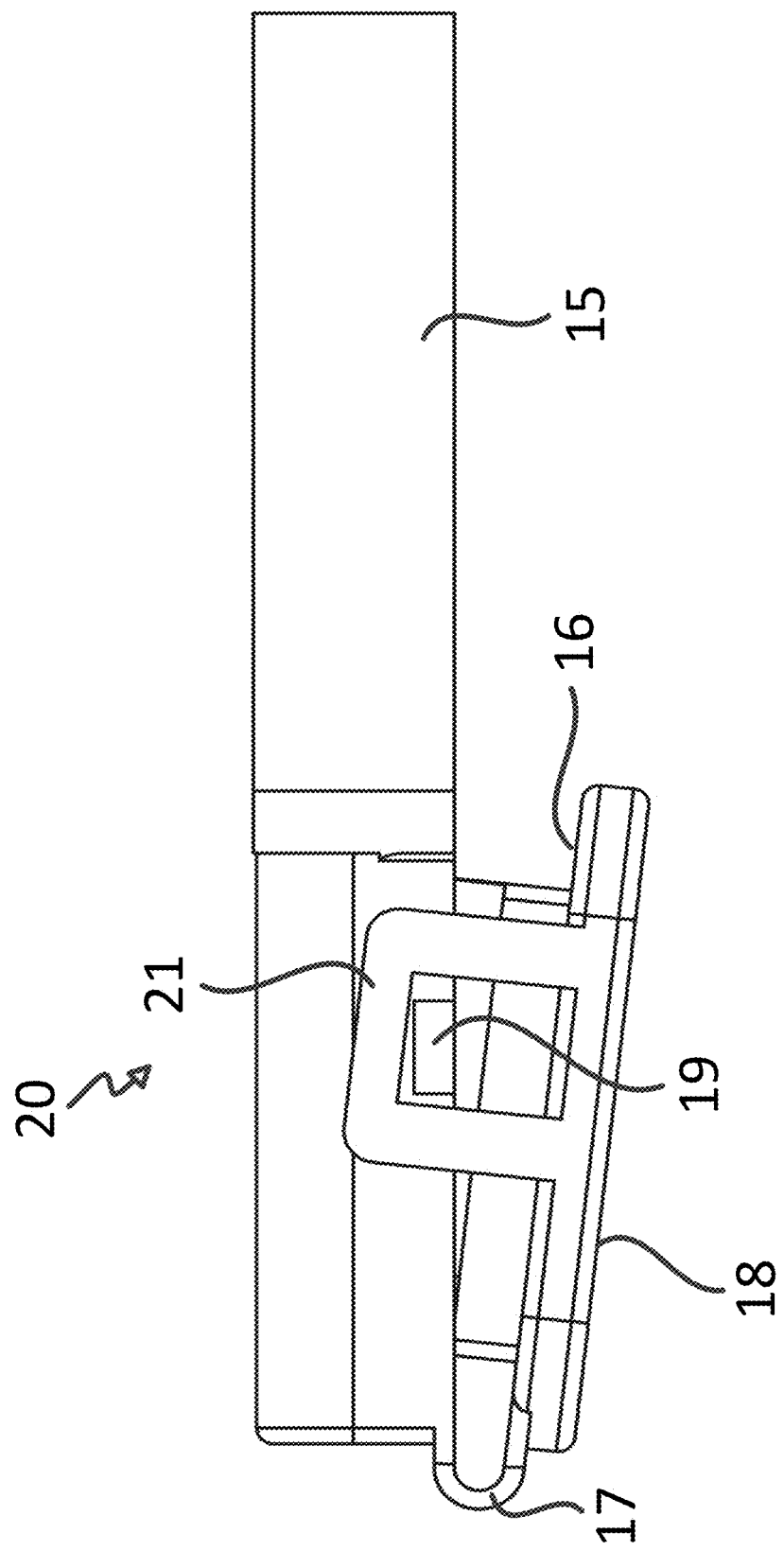
FIG. 3 is a side view of the bending assembly according to the first embodiment of the present invention.
Figure 4:
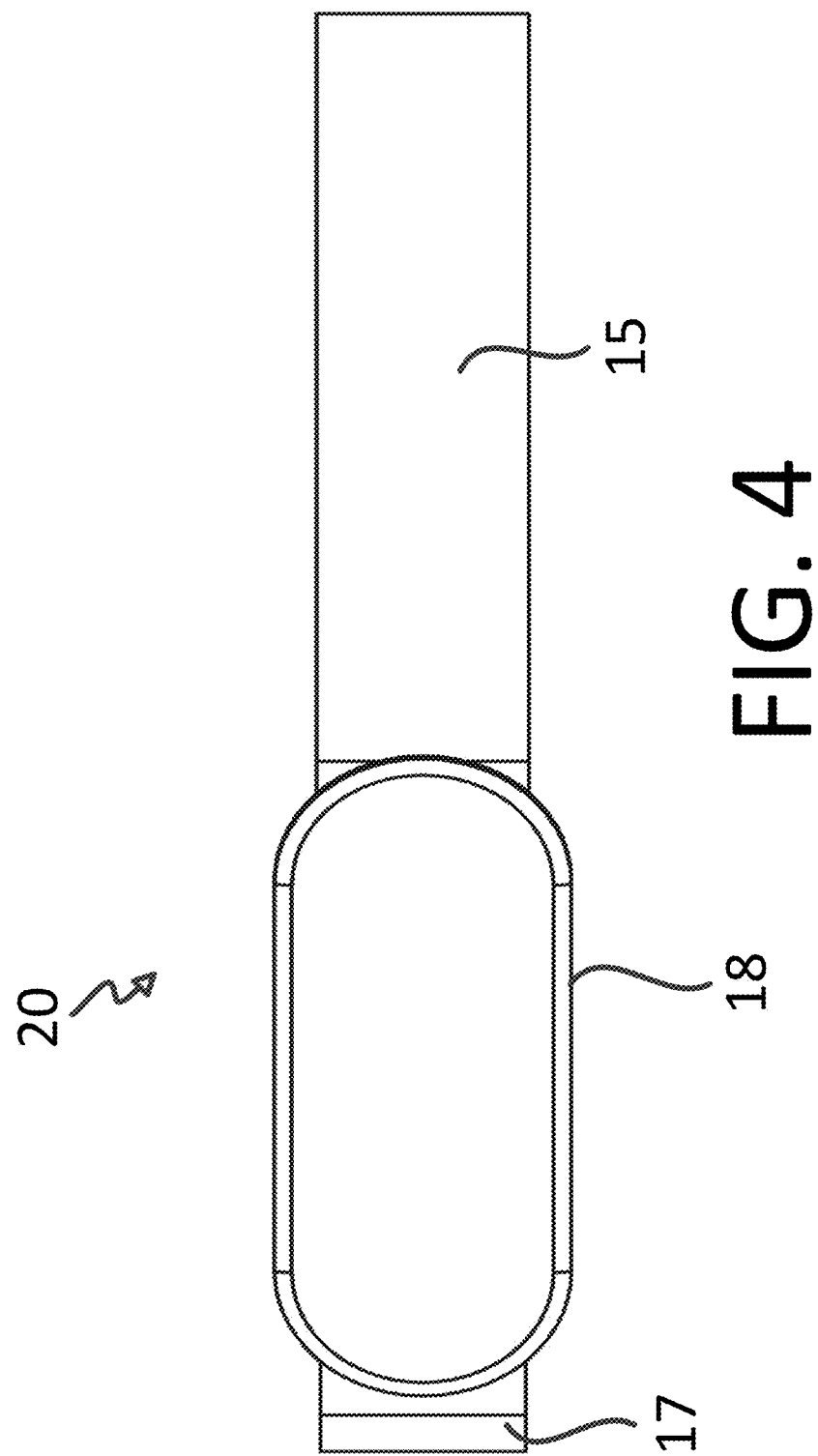
FIG. 4 is a bottom view of the bending assembly in a ready to use configuration according to the first embodiment of the present invention.
Figure 5:
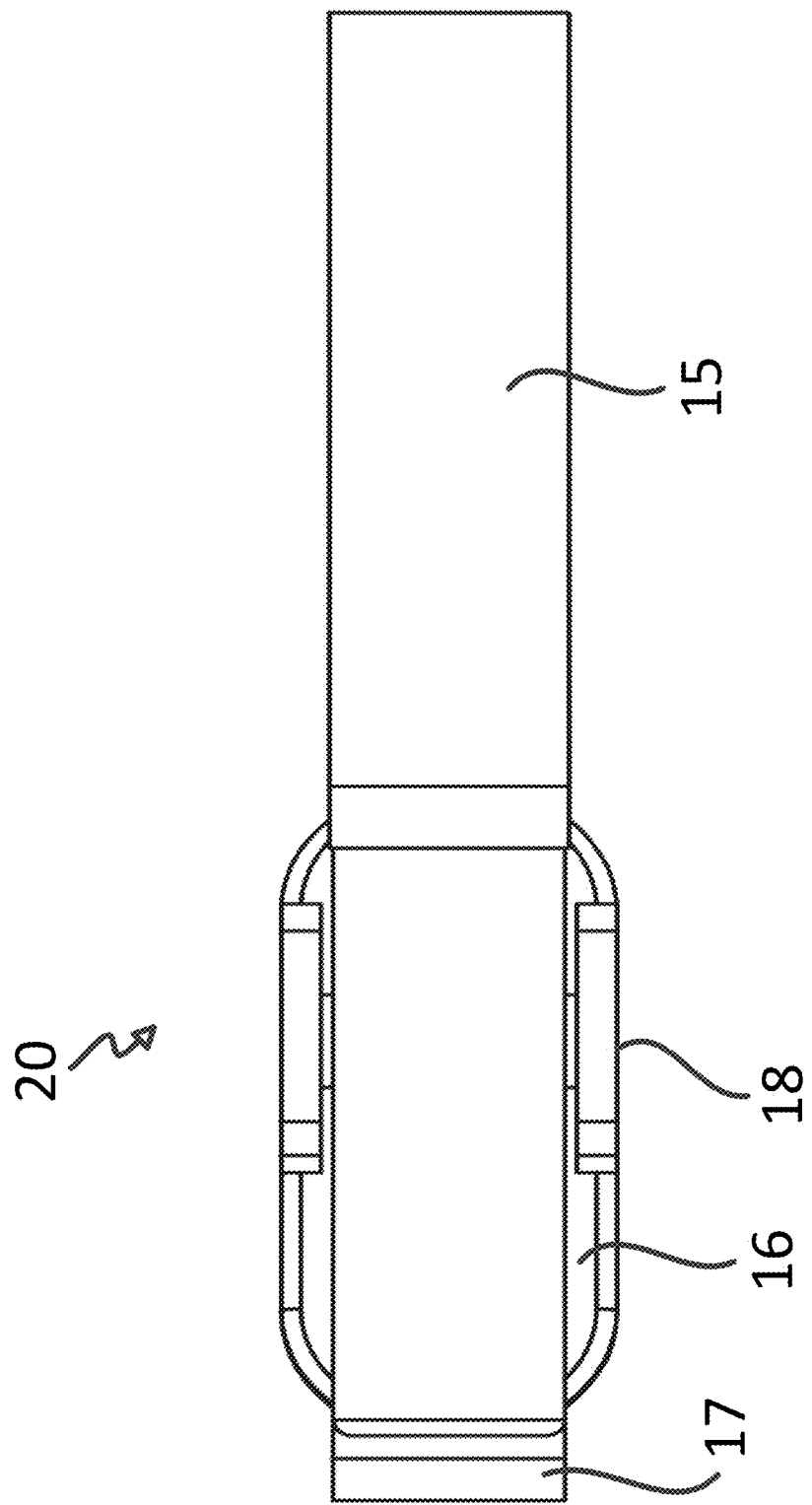
FIG. 5 depicts a top view of the bending assembly in a ready to use configuration according to the first embodiment of the present invention.
Figure 6:
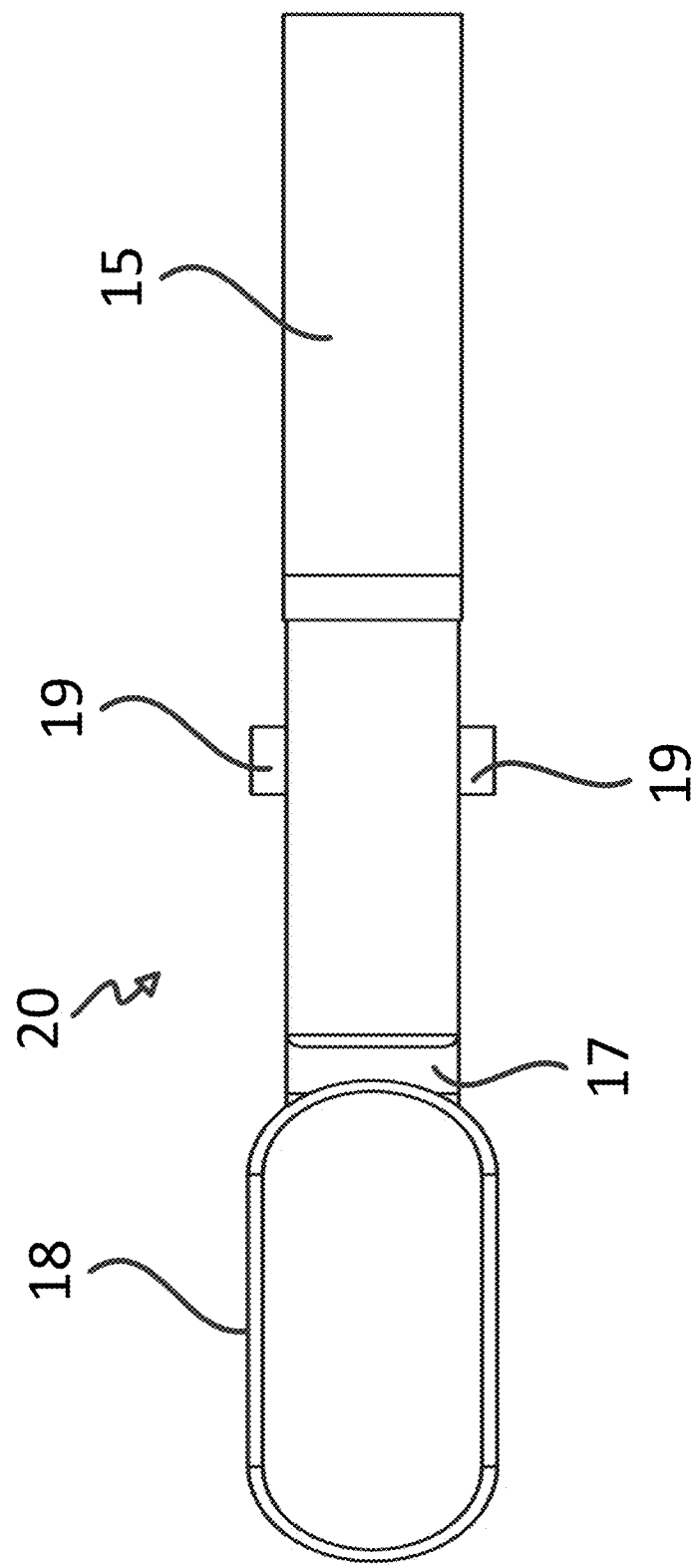
FIG. 6 presents a top view of the bending assembly in an open configuration according to the first embodiment of the present invention.
Figure 7:
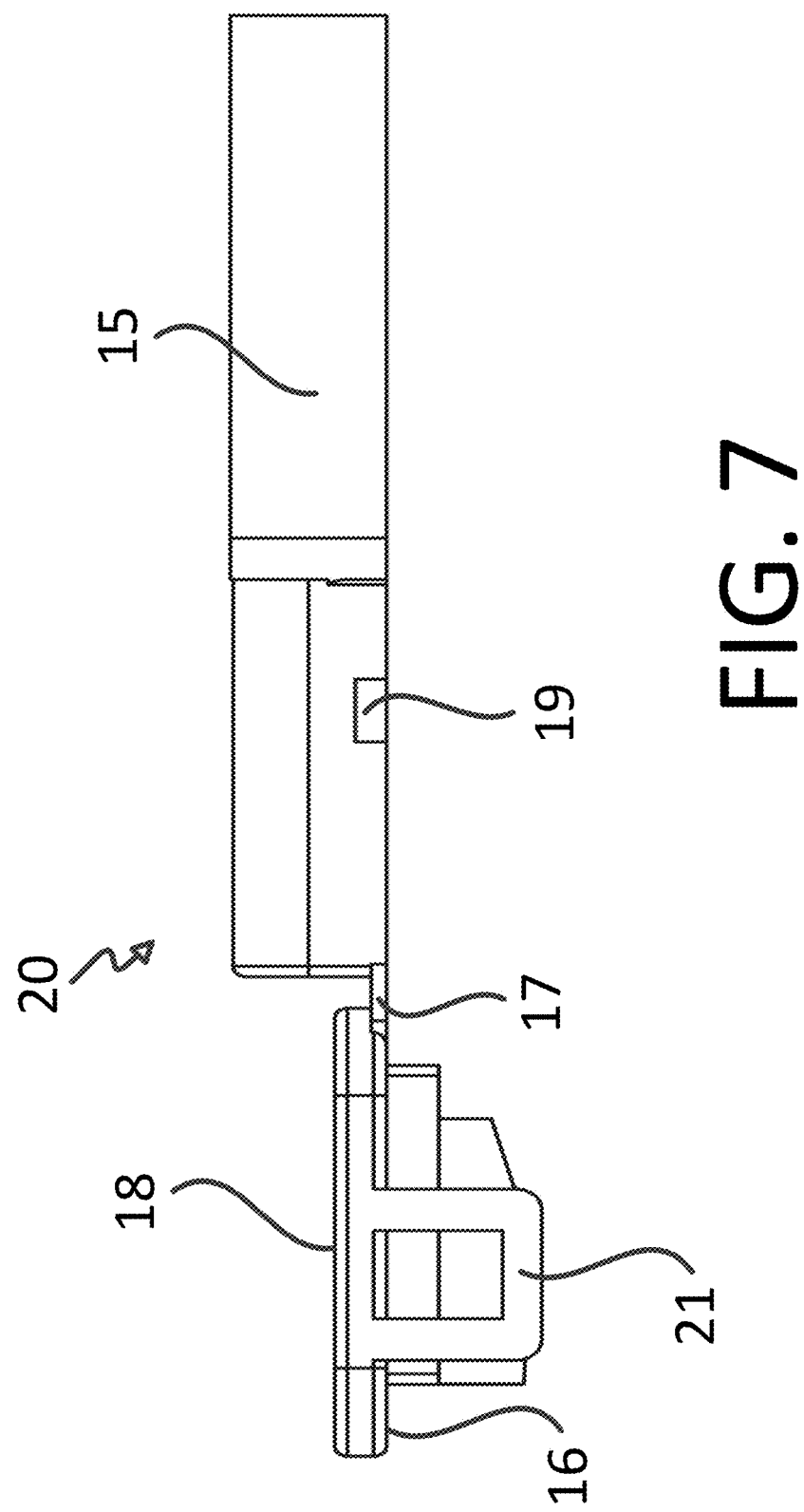
FIG. 7 portrays a side view of the bending assembly in an open configuration according to the first embodiment of the present invention.
Figure 8:
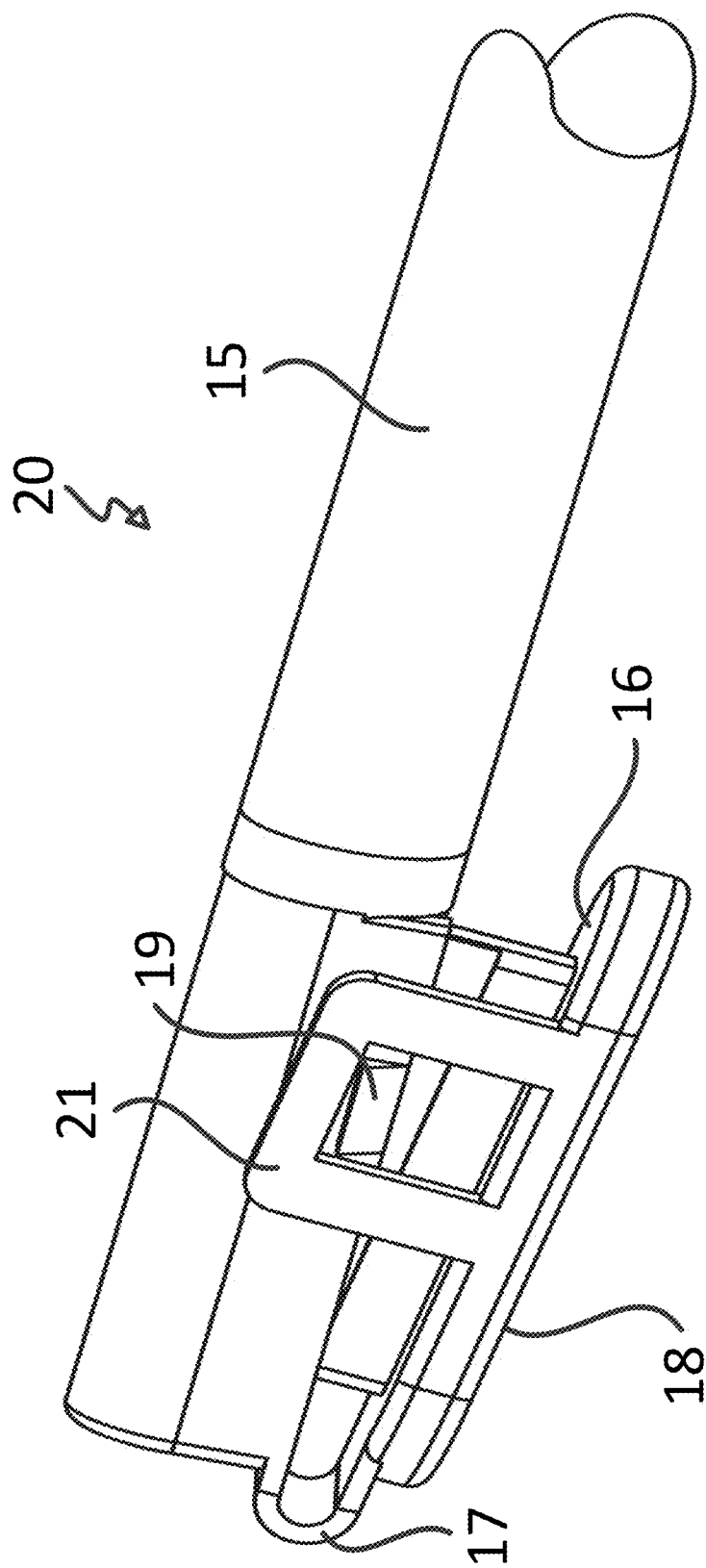
FIG. 8 is a side perspective view of the bending assembly in a ready to use configuration according to the first embodiment of the present invention.
Figure 9:
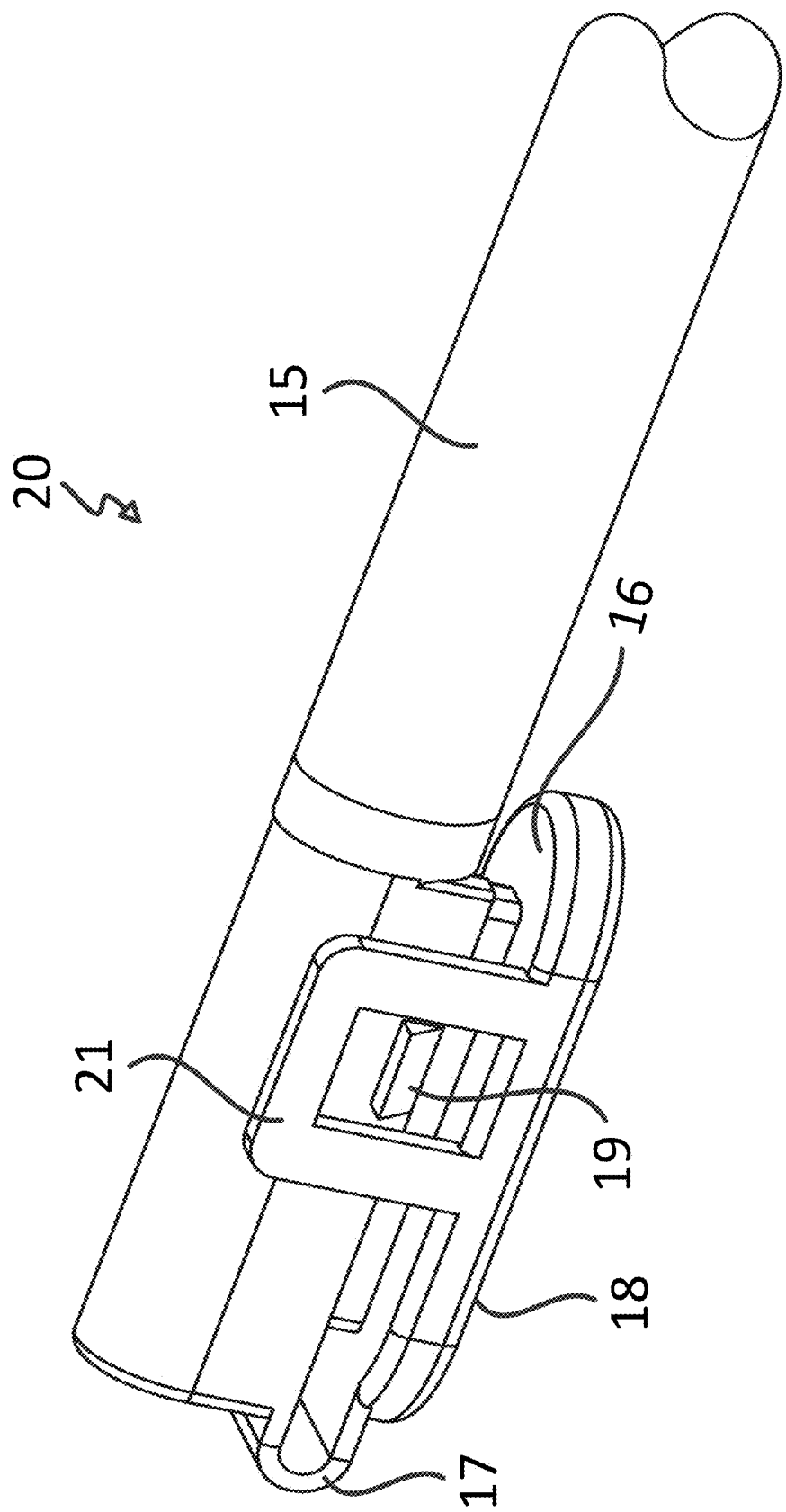
FIG. 9 is a side perspective view of the bending assembly in an after-use configuration according to the first embodiment of the present invention.
Figure 10:
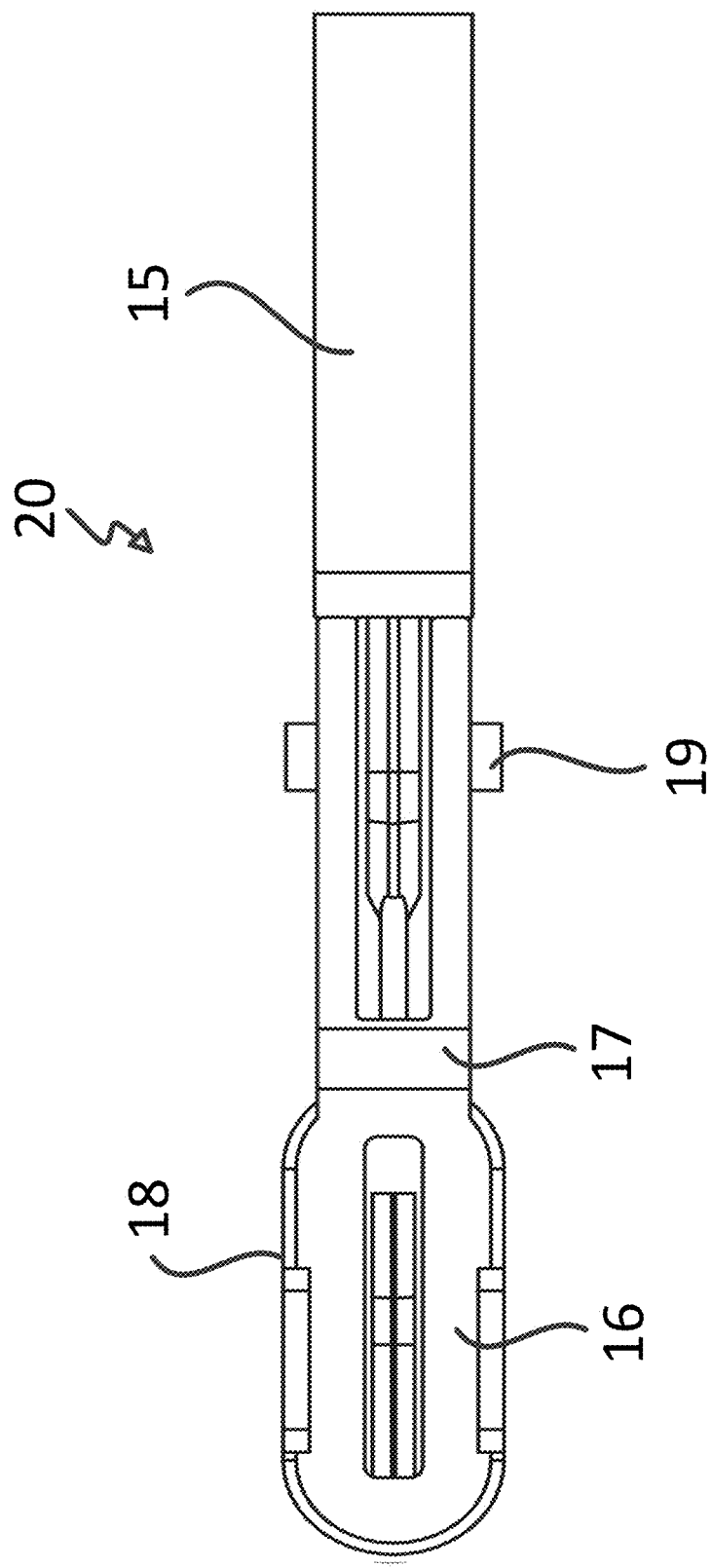
FIG. 10 shows a bottom view of the bending assembly in a fully open configuration according to the first embodiment of the present invention.
Figure 11:
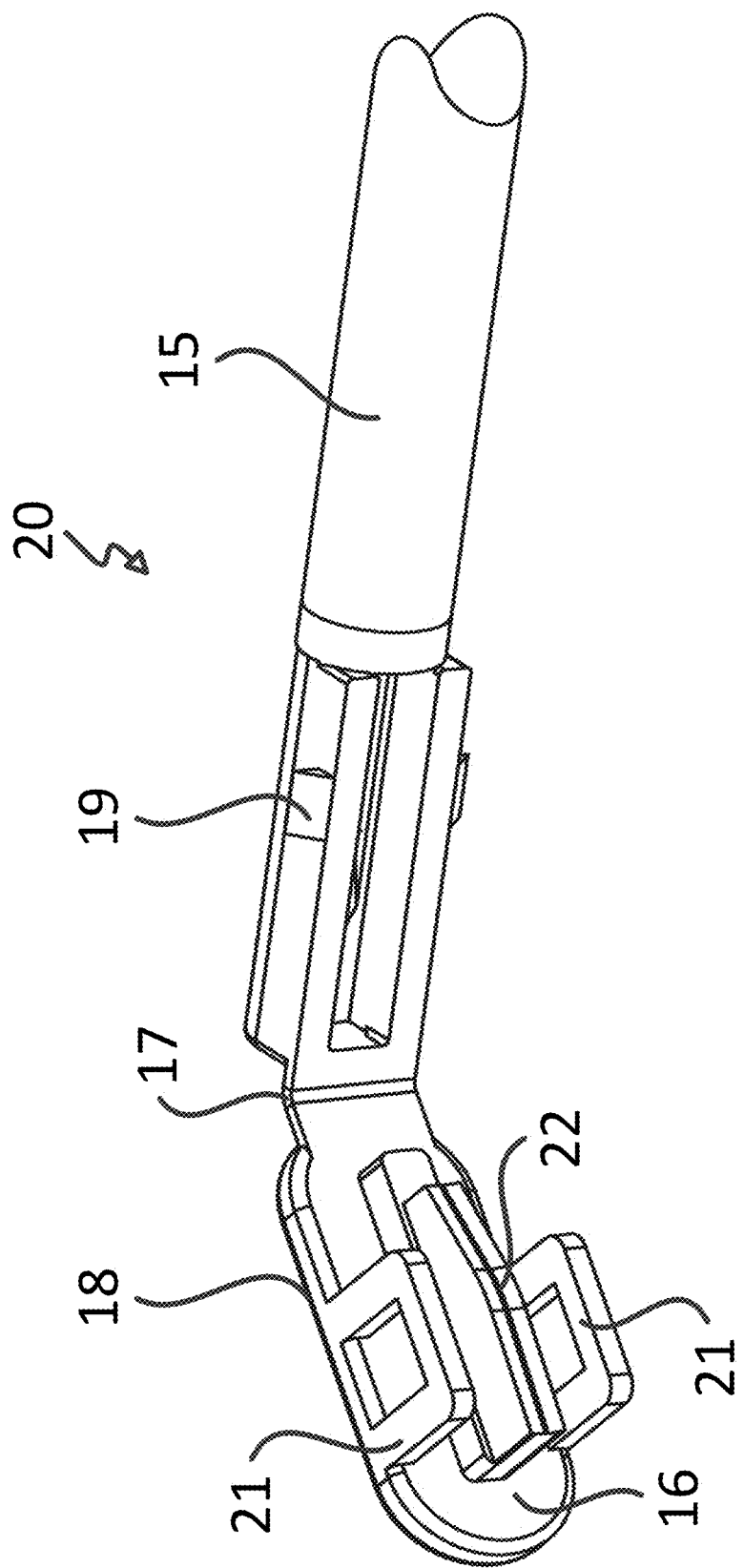
FIG. 11 is a bottom perspective view of the bending assembly in a semi open configuration according to the first embodiment of the present invention.
Figure 12:
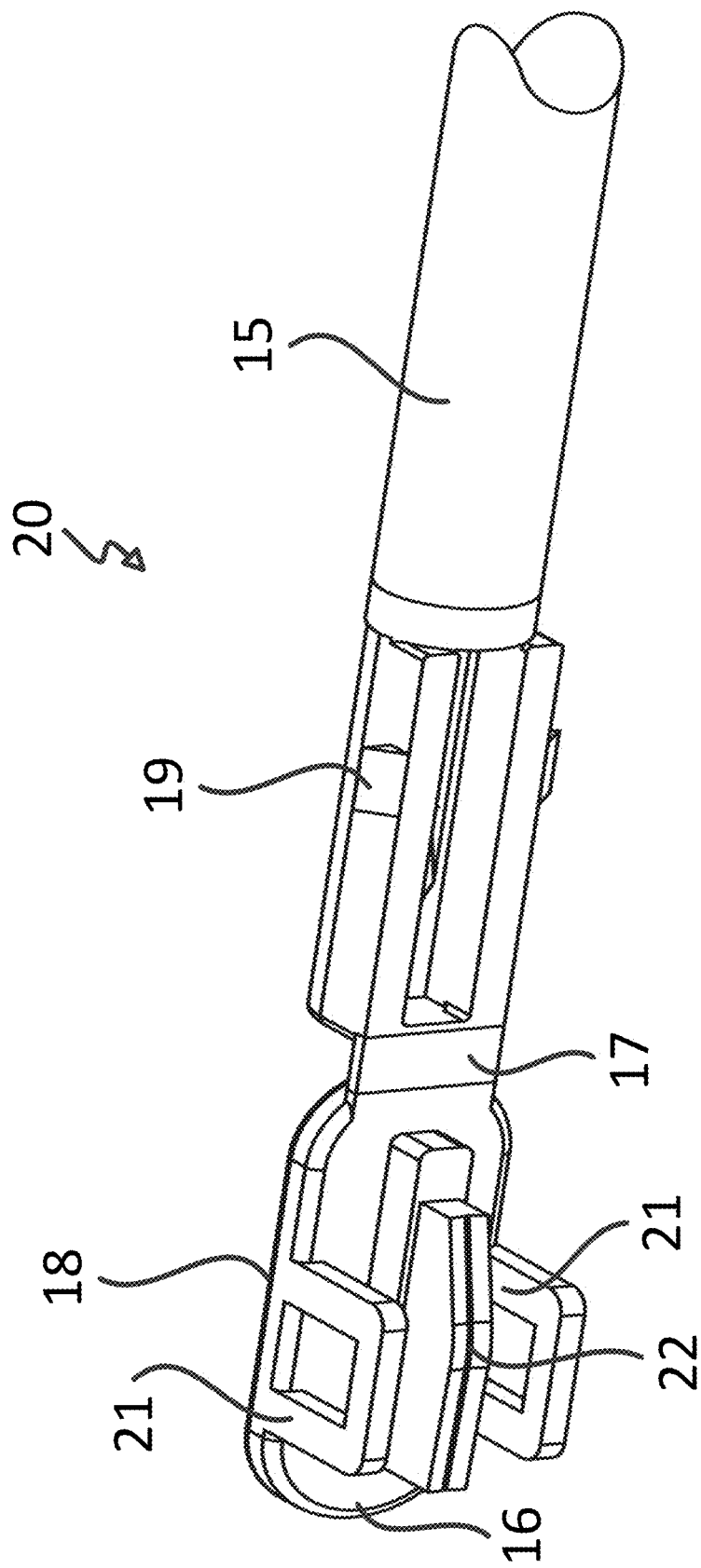
FIG. 12 portrays a second bottom perspective view of the bending assembly in a fully open configuration according to the first embodiment of the present invention.

The first embodiment of the needle bending assembly is illustrated in FIGS. 1-20. A straight hollow needle 11A that requires bending to a distinct angle is wedged at the back end into a needle hub 12. Generally spinal needles have a beveled proximal edge; however, other proximal edge shaped needles also fall within the scope of the present invention. A stylet 13 is threaded into the hollow core of the needle 11A. The back end of the stylet 13, typically a thin metal wire, is contained in a holder 14 that enables the user to grip the stylet 13 direct its movement and remove the stylet 13 once the needle bevel 72 is at its intended target location. Likewise, the needle hub 12 enables the user to grip the needle 11A and direct its movement. The combination of the needle 11A and stylet comprise the needle assembly 10 as shown in FIG. 1. The bending assembly 20 comprises the needle 11A assembly combined with housing 15 and bending member 18. Built into the bending member 18 are base 16 and fulcrum 22 disposed on the base 16. The proximal end of the housing 15 is open at the bottom and the fulcrum 22 is configured to fit into the opening. The housing 15 contains and envelopes the needle 11A and includes the proximal bending section and the distal section of the needle 11A. It is noted that the holder 14 contains a keying feature 71 that matches the bevel 72 on the needle 11A tip and enables precise orientation during the manufacturing of the assembly.

The bending member 18 is attached to the bending assembly housing 15 using flexible hinge 17 that enables pivoting movement of the bending member 18 from a position of being attached to the housing 15 to a position 180 degrees away from the housing 15. The bending assembly housing 15 contains an angled barrier wall 24 contoured to the shape of the bent needle 11B shape. In the pre-use or ready to use configuration, needle 11A is positioned and held in place by the needle hub 12 and supported by an edge 29 of the barrier wall 24 located above the needle and fulcrum 22 located below the needle. The bending member 18 is held in place with the fulcrum 22 in contact with the needle 11A by locking arms 21 being engaged by locking tabs 19. The bending assembly is packaged in a ready to use configuration as shown in FIGS. 4, 5, 8, 13-5 and 17. To further secure the stability of the assembly in transportation, a rib 23 is placed onto a collar 25 located at the interface between the bending member 18 and housing 15 that prevents rotational movement of the bending member that may result in the needle shifting out of position.

The unbent needles inside the housing used in this application generally have a 22-25 gauge and vary in length from about 76 mm to about 178 mm. The unbent needles may be removed intact from the housing if the medical procedure requires a straight needle.

Figure 13:
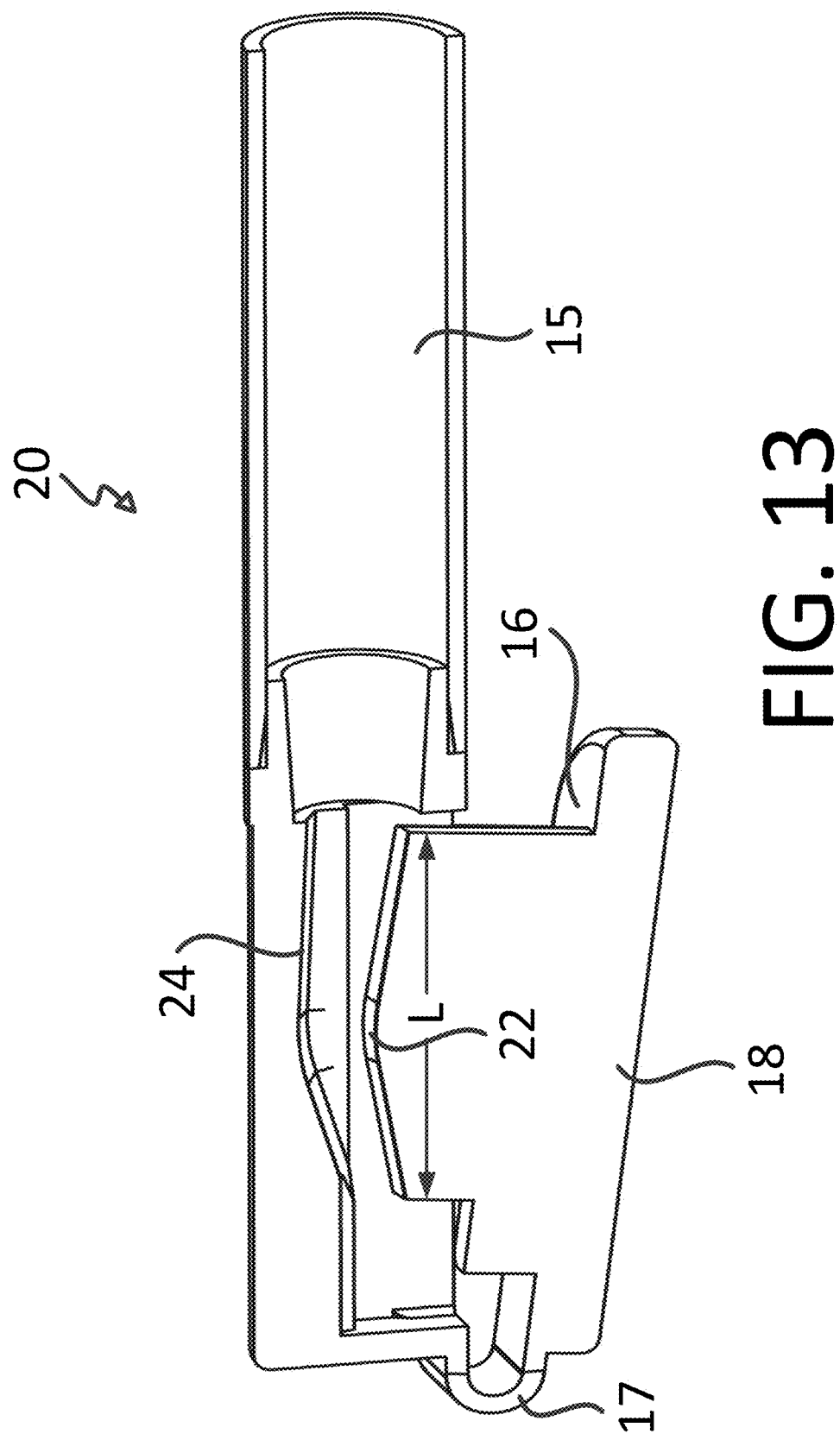
FIG. 13 is a perspective cross sectional side view of the bending assembly without the needle in a ready to use configuration according to the first embodiment of the present invention.
Figure 18:
FIG. 18 shows the bent needle removed from the bending assembly according to the first embodiment of the present invention.
Figure 19:
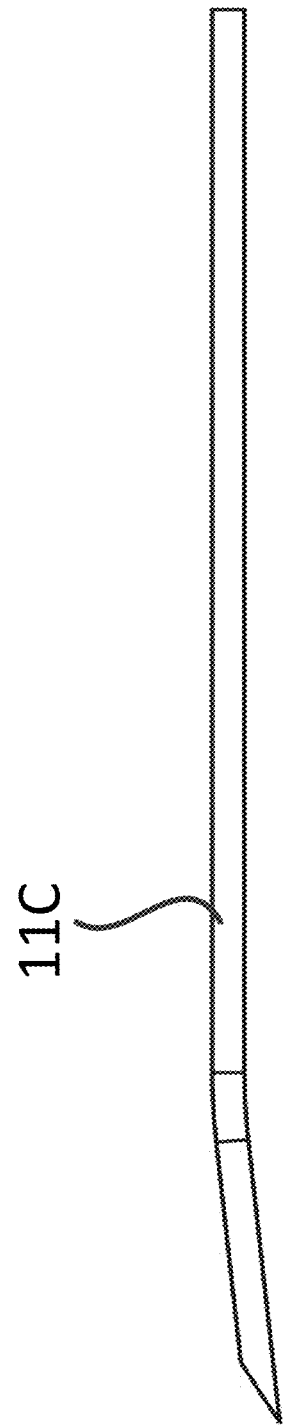
FIG. 19 shows the bend needle after relaxation according to the first embodiment of the present invention.
Figure 20:
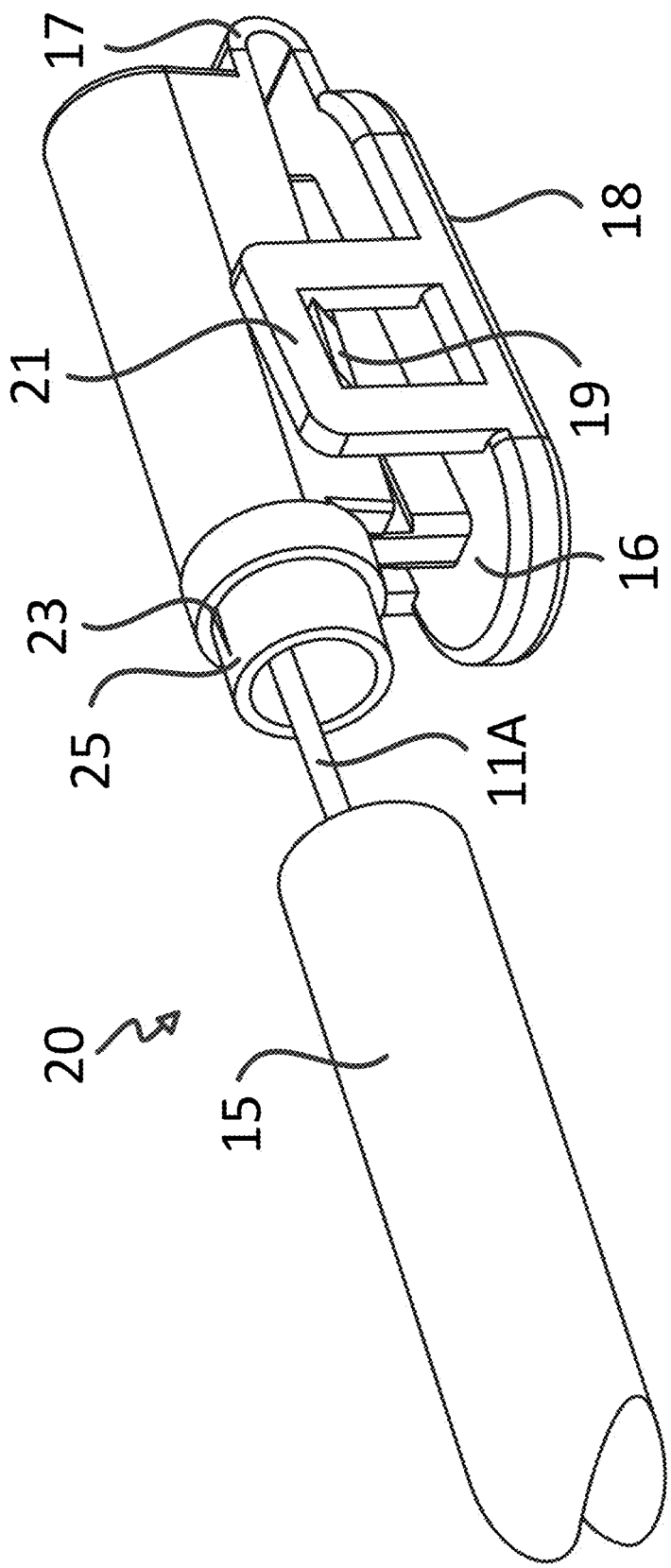
FIG. 20 depicts a perspective view of the bending assembly containing a structure stabilizing component according to the first embodiment of the present invention.
Figure 21:
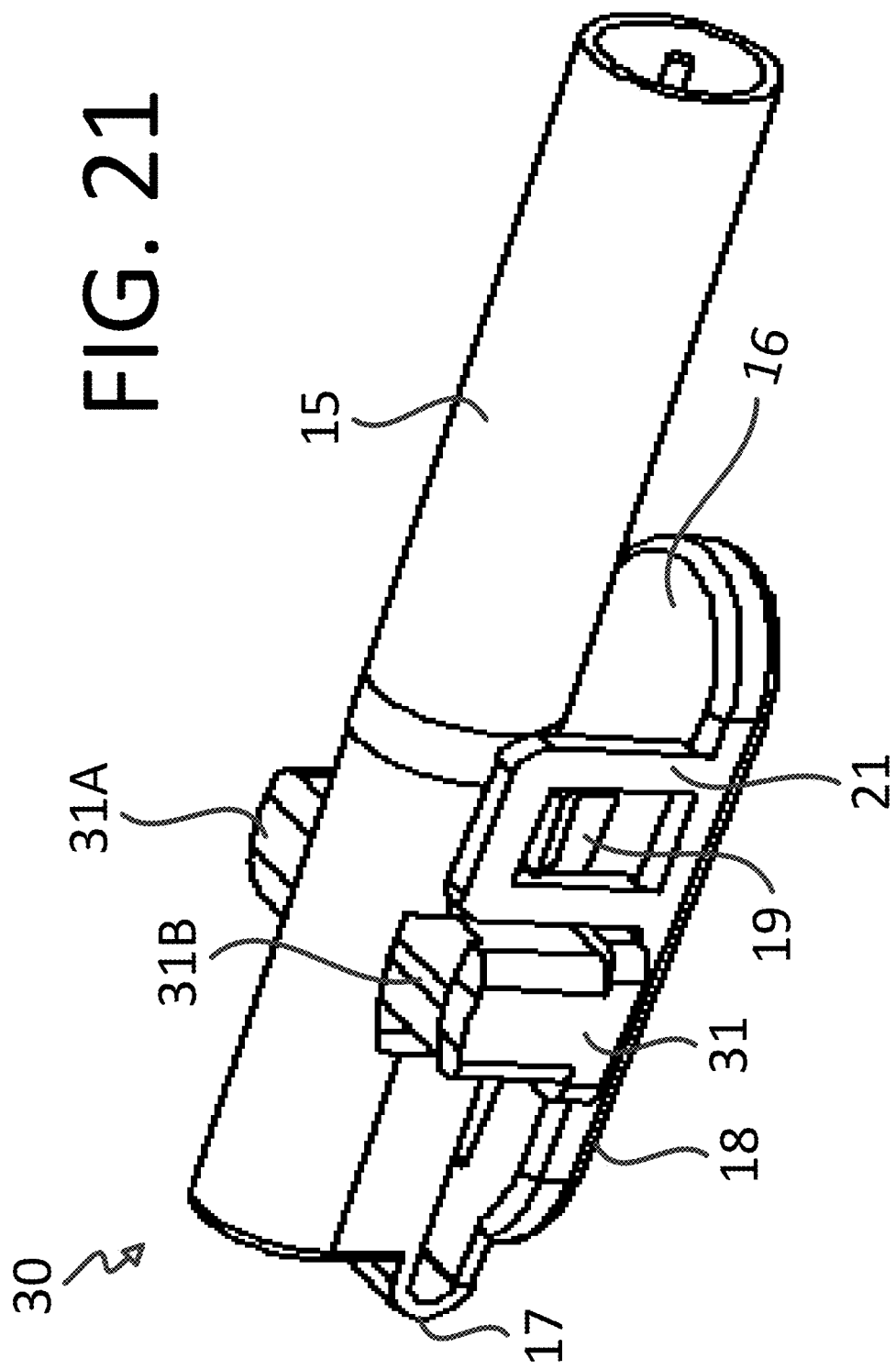
FIG. 21 shows a perspective view of a bending assembly according to a second embodiment of the present invention.
Figure 22:
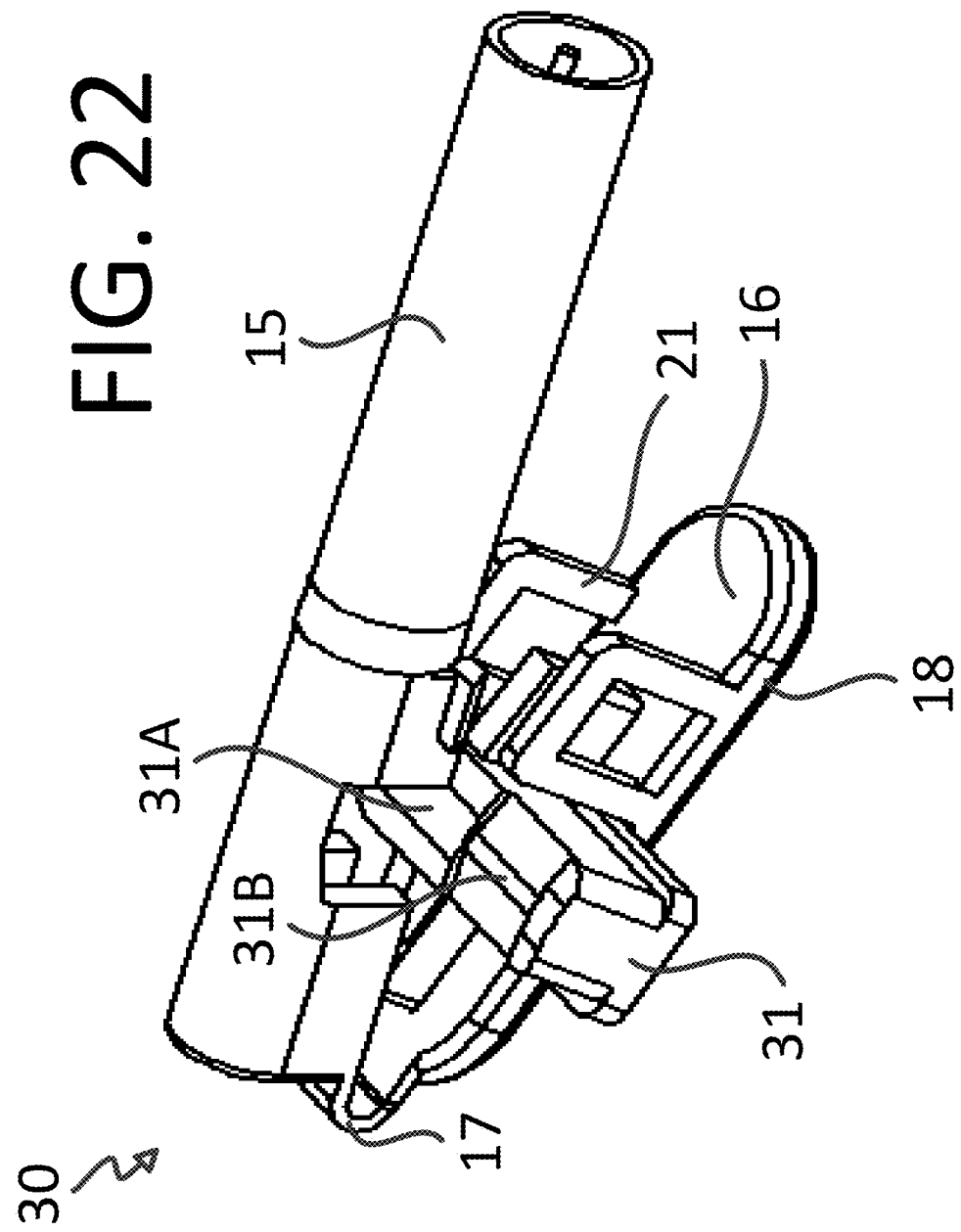
FIG. 22 illustrates a side perspective view of the bending assembly according to the second embodiment of the present invention.
Figure 23:
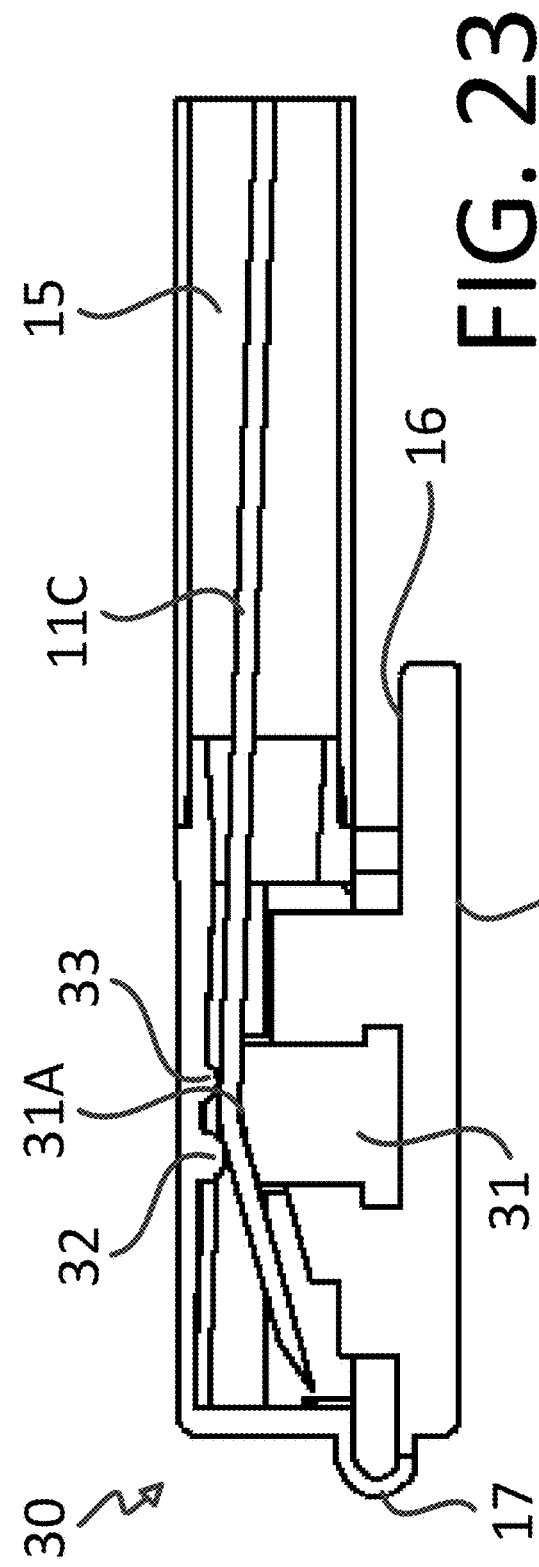
FIG. 23 depicts a cross sectional side view of the bending assembly showing the bent needle in a first after-use configuration according to the second embodiment of the present invention.
Figure 24:
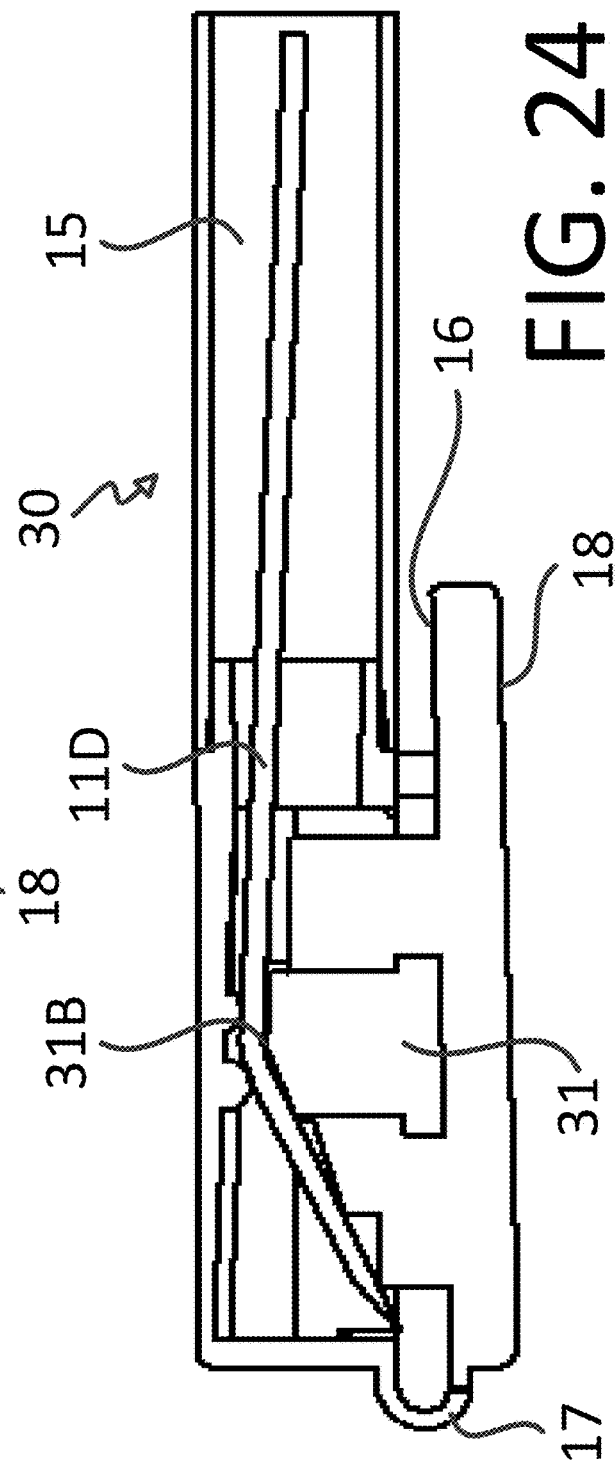
FIG. 24 shows a cross sectional side view of the bending assembly showing the bent needle in a second after-use configuration according to the second embodiment of the present invention.
Figure 25:
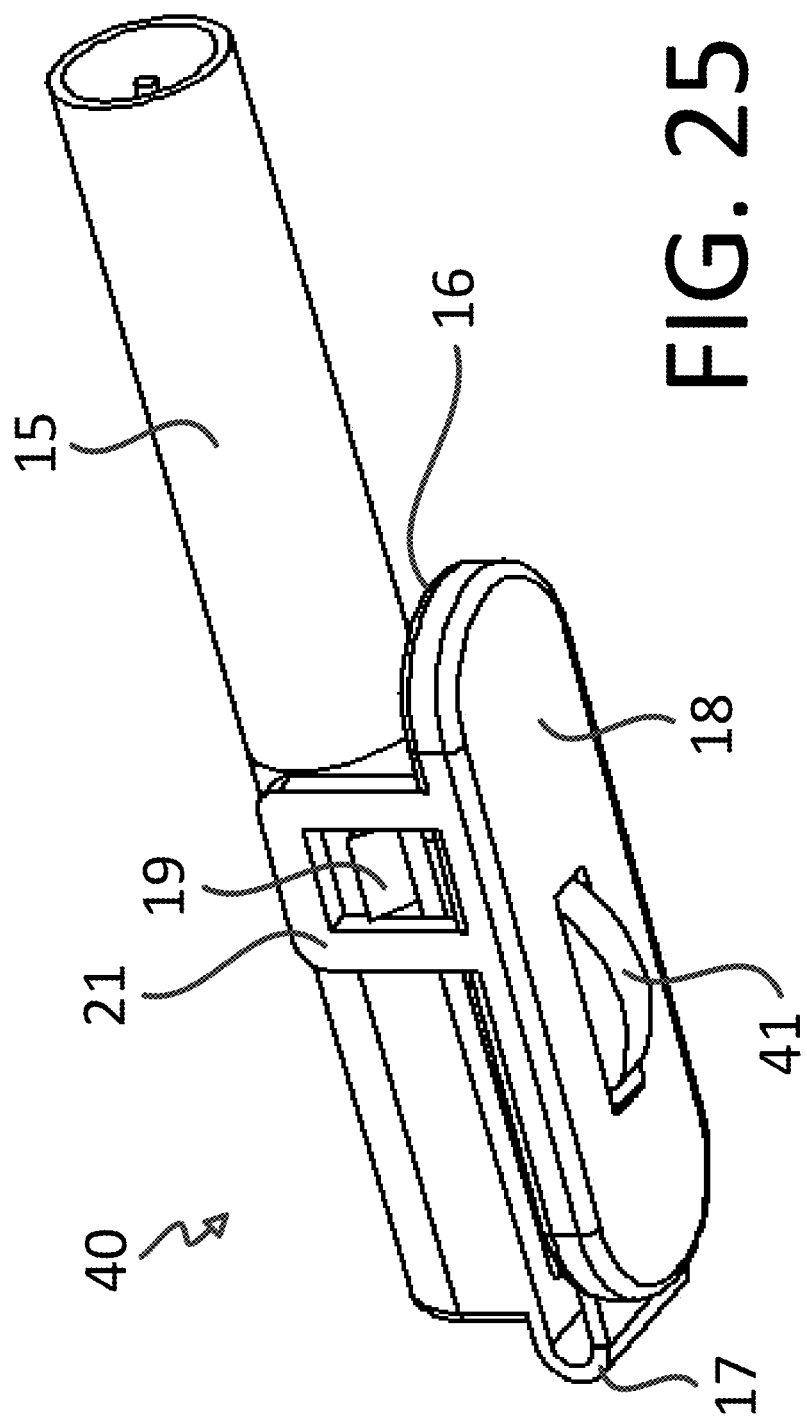
FIG. 25 presents a bottom side perspective view of a bending assembly according to a third embodiment of the present invention.
Figure 26:
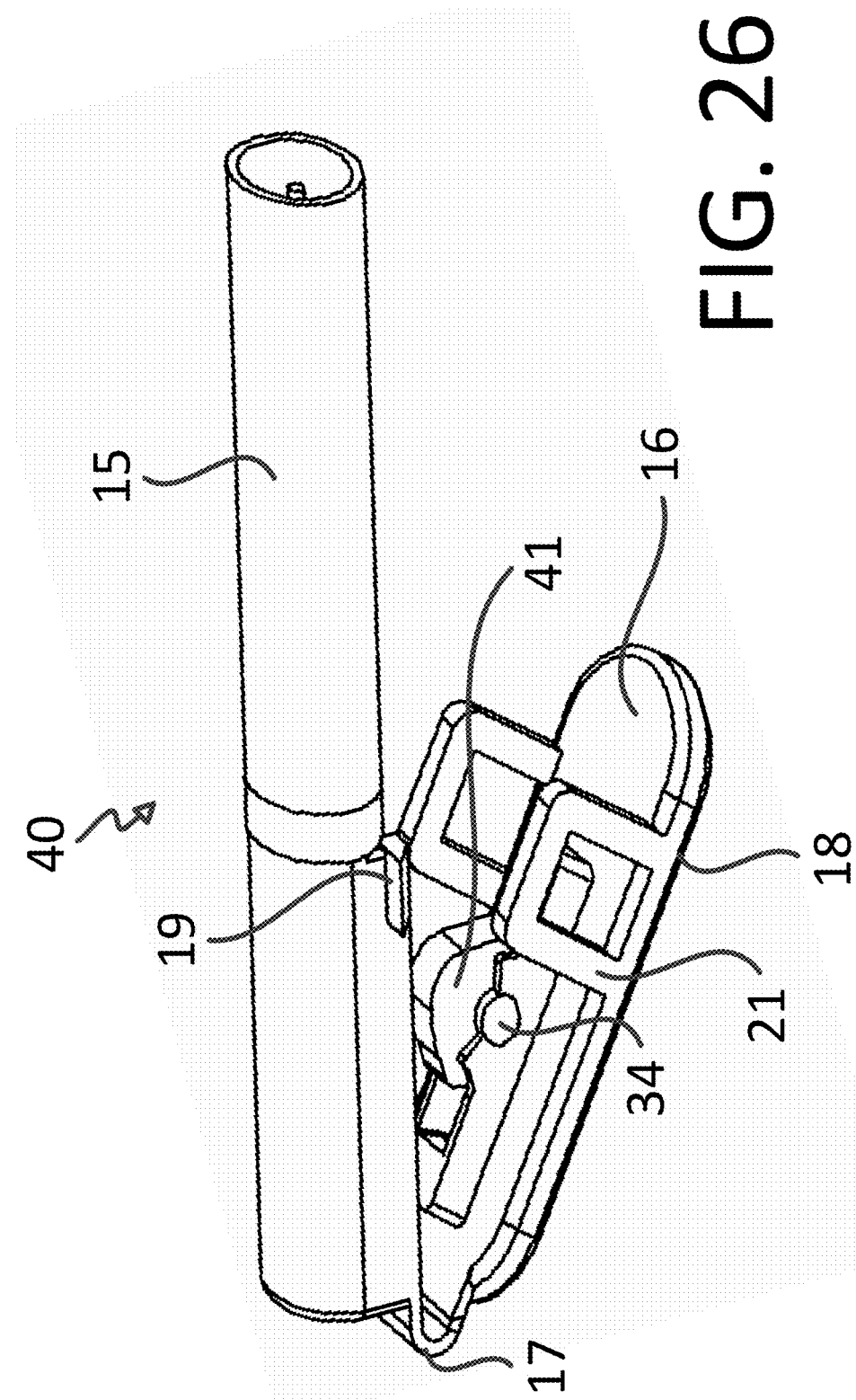
FIG. 26 illustrates a top and side perspective view of the bending assembly according to the third embodiment of the present invention.

The bending would be applied along a designated length at a distance of about 0.9 cm to 1.1 cm from the proximal edge of the needle onto which the fulcrum 22 is positioned. The bending angle ranges from about 19 to 23 degrees. The force required to achieve the bending depends on the length and shape of the barrier wall and the corresponding length and shape of the momentum arm, i.e. the fulcrum that is used to achieve the bending. This length, L, is shown in FIG. 13. Experimental results indicate that for a fulcrum length, L, of between 1.27 cm to about 3.81 cm, the required bending force ranges from about 1.36 kg-force to about 7.26 pound-force. After the needle is bent, it is removed from the bending assembly. The needle then undergoes a metal relaxation phase that reduces the angle by about 15 degrees. A needle that has undergone metal relaxation 11C is shown in FIG. 19. Generally speaking, a needle that needs to have a final 5-degree bent, must initially be bent to about 20 degrees. Likewise, if the user requires a needle having a 7-degree bend, the target angle for the initial bending should be 22 degrees, although there may be differences based on spinal needle manufacturer, wall thickness and other material properties that may require a target initial bend angle of between 19 to about 23 degrees.

The steps of bending the needle using the needle bending assembly of the present invention are as follows:

1. Pinching the base of the bending member toward the needle using one's thumb and index finger. This will result in the fulcrum bending the needle to the angle into the shape of the fulcrum and the barrier wall. The movement will stop when the bent needle is pressed by the bending member against the barrier wall which then prevents further movement. Typically, thumb pressure is applied; however, other means for applying pressure also fall within the scope of the present invention as needed.

2. Releasing the pinching pressure and removing the needle from the housing and removing the needle assembly from the bending assembly. The angle of the needle will initially match that of the fulcrum and the barrier wall configured in the range of 19 to about 23 degrees but will relax to an angle of 5 to 6 degrees almost instantaneously once pressure is relaxed.

In a typical medical procedure requiring a bent spinal needle, the user inserts the bent needle that contains the stylet into the into the human body, twisting the needle about its long axis as needed for steering. This metal stylet or wire fills the internal diameter of the spinal needle during insertion in the body, preventing tissue or fluid blockage. Once the tip is at its intended position, the stylet is removed and anesthetic, steroid, antibiotic, contrast agent or other therapeutic agent can be injected or spinal fluid can be removed, as is done for lumbar puncture.

A second embodiment 30 for a needle bending assembly is depicted in FIGS. 21-24. As in the first embodiment, the proximal end of the housing 15 is open at the bottom and comprises a needle bending member 18 that contains a base 16 and locking arms 21 being engaged by locking tabs 19. The needle bending member 18 is attached to the bending assembly housing 15 using flexible hinge 17 that enables pivoting movement of the bending member 18 from a position of being attached to the housing 15 to a position 180 degrees away from the housing 15. The needle bending assembly comprises an anvil 31 that is attached to the top inner surface of the base 16 and is configured to fit inside the opening of the housing 15. The top surface of the anvil 31 contains two sections: a first section contoured at a relatively shallow angle of 19 to about 23 degrees and defined by fulcrum 31A and a second section contoured at a relatively steep angle of 24 to about 28 degrees defined by fulcrum 31B. The top surface of the anvil 31 is configured to contact and support the needle 11A in a similar manner to that of the fulcrum 22 in the first embodiment prior to applying pressure that bends the needle 11A, The bending would be applied at a designated spot on the needle 11A at a distance of about 0.9 cm to 1.1 cm from the proximal edge of the needle onto which the fulcrum, 31A or 31B, is positioned.

The anvil 31 is configured to slide in perpendicular to the housing. This action enables the user to bring the desired section of the anvil 31 in contact with the straight needle 11A and to bend the needle 11A to a range of either 19 to about 23 degrees as shown by 11C in FIG. 23 or to a range of 24 to about 28 degrees as shown by 11D in FIG. 24. The ranges reflect differences in spinal needles depending on the manufacturers, wall thickness and other material properties.

To bend the needle 11A, the user would select the desired section to contact the needle 11A and apply thumb pressure onto the bottom of the base. The fulcrum of that section in contact with the designated spot on the needle 11A will transfer the pressure and bend the needle. Two knobs 32 and 33 attached to an inner wall of the housing serve as barriers against which the needle is bent to prevent needle overbending from the pressure exerted by the anvil 31. The knobs 32 and 33 are sized and spaced in such a way as to accommodate both the relatively shallow angle of 19 to about 23 degrees or the steeper 24 to about 28 degrees angle. Of note is that the larger knob 32 is configured to shape the bent section of the needle 11C or 11D, while the smaller knob 31 is configured to support the unbent section of the needle 11C or 11D. Also, of note is that the spacing between knobs 31 and 32 is adapted to accommodate the needle 11D apex of the steeper angle 31B.

A short time after a needle is bent, the bent needle undergoes metal relaxation that reduces its angle by about 15 degrees. Thus, a needle bent to 19 to about 23 degrees generally relaxes to about 5 to about 6 degrees, while a needle bent to 24 to about 28 degrees generally relaxes to about 10 to about 12 degrees depending on the material properties of the needle being bent. It is noted that anvils containing more than two contoured top surface sections also fall within the scope of the present invention.

A third embodiment 40 for a needle bending assembly is depicted in FIGS. 25-28. As in the first embodiment, the proximal end of the housing 15 is open at the bottom and comprises a needle bending member 18 that contains a base 16 and locking arms 21 being engaged by locking tabs 19. The needle bending member 18 is attached to the bending assembly housing 15 using flexible hinge 17 that enables pivoting movement of the bending member 18 from a position of being attached to the housing 15 to a position 180 degrees away from the housing 15. The needle bending assembly comprises a wheel 41 attached to the bending member 18 by way of pivoting pin 34. The outer circumference of the wheel 41 contains a first section 41A contoured at a relatively shallow angle of 19 to about 23 degrees and a second section 41B contoured at a relatively steep angle of 24 to about 28 degrees.

Each section of the wheel 41 is configured to contact and support the unbent needle 11A in a similar manner to that of the fulcrum 22 in the first embodiment prior to applying pressure that bends the needle 11A. The wheel 41 is configured to pivot from a position of the fulcrum of the first angle 41A being in contact with the designated spot of the needle 11A to a position of the fulcrum 41B of the second angle being in contact with the designated spot of the needle 11A. This action enables the user to bring the desired section of the wheel 41 in contact with the needle 11A and to bend the needle 11A to a range of either 19 to about 23 degrees as shown by 11E in FIG. 27 or to a range of 24 to about 28 degrees as shown by 11F in FIG. 28. The ranges reflect differences in spinal needles depending on the manufacturers, wall thickness and other material properties.

To bend the needle 11A, the user would turn the wheel 41 such that the fulcrum of the desired angle, 41A or 41B, be positioned onto the designated spot of the needle 11A. The user would then apply thumb pressure onto the bottom of the base 16. The fulcrum in contact with the designated spot on the needle 11A will transfer the pressure and bend the needle.

As in the second embodiment, a first knob 32 and a second knob 33 attached to an inner wall of the housing serve as barriers against which the needle is bent to prevent needle overbending from the pressure exerted by the fulcrum. The knobs 32 and 33 are sized and spaced in such a way as to accommodate both the relatively shallow angle of 19 to about 23 degrees or the steeper 24 to about 28 degrees angle. Of note is that knob 32 is larger than knob 31 and is configured to shape the bent section of the needle, and the spacing is configured to accommodate the apex of the steeper angle 41B.

A short time after a needle is bent, the bent needle undergoes metal relaxation that reduces its angle by about 15 degrees. Thus, a needle bent to 19 to about 23 degrees generally relaxes to about 5 to about 6 degrees, while a needle bent to 24 to about 28 degrees generally relaxes to about 10 to about 12 degrees. It is noted that a wheel containing more than two contoured circumference sections also fall within the scope of the present invention.

The second and third embodiments provide the user with the option to produce a needle having a 5 to about 6 degree bent or a needle having a 10 to about 12 degree bent to be used in a different application as needed.

It should be understood, of course, that the foregoing relates to exemplary embodiments of the invention and that modifications may be made without departing from the spirit and scope of the invention.

We claim:

1. A needle bending assembly comprising:
a housing containing a needle, the needle having a hollow core, said housing and said needle having a proximal end and a distal end, said distal end of the needle being supported by a needle hub containing the distal end of the needle, said proximal end of the needle being supported by an upper wall portion of the housing, the proximal end of the housing having a bottom opening; and
a bending member configured to fit in the bottom opening and to support the proximal end of the needle, said bending member having a shape of an angle containing a fulcrum configured for applying pressure onto a designated spot of the needle between the proximal end and the distal end of the needle, said pressure resulting in bending the needle to a shape of the angle of the bending member.

2. The needle bending assembly of claim 1 further comprising a stylet inserted into the hollow core of the needle.

3. The needle bending assembly of claim 2, wherein the fulcrum is contoured at an angle ranging from 19 to about 23 degrees and wherein a force of 1300 grams to about 1700 grams applied onto the bending member is configured to bend the needle having a gauge in the range of 22 to 25, said designated spot being at a distance of between 0.9 cm to about 1.1 cm from a tip of the needle.

4. The needle bending assembly of claim 2, further comprising a barrier disposed inside the housing against which the fulcrum presses the needle, the barrier having a contour of the fulcrum, said barrier being configured to prevent overbending of the needle.

5. The needle bending assembly of claim 2, wherein the fulcrum is disposed onto a base, said base being hingedly attached to the housing in a manner that the base is pivotable from an open position away from the housing to a closed position configured for supporting and bending the needle.

6. The needle bending assembly of claim 5, further comprising a collar in the housing, said collar containing a rib for preventing rotational movement of the bending member at an interface.

7. A method for manufacturing a bent needle the method comprising:
a) providing the needle bending assembly of claim 6;
b) applying pinching force onto the bending member base toward the needle to move the base until it comes to a stop;
c) releasing the pinching force and allowing for needle relaxation;
d) removing the bent needle from the housing; and
e) allowing for needle angle relaxation.

8. The needle bending assembly of claim 2, further comprising locking tabs disposed on outer walls of the housing configured to engage locking arms attached to a base of the bending member.

9. A needle bending assembly comprising:
a housing containing a needle, the needle having a hollow core, said housing and said needle having a proximal end and a distal end, said distal end of the needle being supported by a needle hub containing the distal end of the needle, said proximal end of the needle being supported by an upper wall portion of the housing, the proximal end of the housing having a bottom opening; and
a dual angle bending member configured to fit in the bottom opening and to support a bottom of the proximal end of the needle, said dual angle bending member having a top surface containing a first section contoured in a shape of a first angle, said first section containing a first fulcrum and a second section contoured in a shape of a second angle, said second section containing a second fulcrum, said dual angle bending member being configured for selecting the first section or the second section for applying bending pressure by the respective fulcrum onto a designated spot of the needle between the proximal end and distal end of the needle, said pressure resulting in overlaying a shape of a selected section of the dual angle bending member onto the needle.

10. The needle bending assembly of claim 9 further comprising a stylet inserted into the hollow core of the needle.

11. The needle bending assembly of claim 10, further comprising a first knob disposed inside the housing, the first knob being placed above the designated spot of the needle and further comprising a second knob disposed inside the housing, said second knob being placed above the designated spot of the needle, said first knob and said second knob providing a counterforce to the bending pressure of the dual angle bending member to shape an angle of the needle to correspond to the contour of the angle of the first or second angle of the selected section.

12. The needle bending assembly of claim 11, wherein the dual angle bending member is attached to a base, wherein the base is hingedly attached to the housing in a manner that the base is pivotable from an open position away from the housing to a closed position configured for supporting and bending the needle.

13. The needle bending assembly of claim 11, further comprising locking tabs disposed on outer walls of the bending assembly configured to engage locking arms attached to a base of the dual angle bending member.

14. The needle bending assembly of claim 12, wherein pressure applied onto the base is adapted for bending the stylet containing the needle having a gauge in the range of 22 to 25 wherein a bending force ranges from about 1,300 to 7,300 grams, the bending forces being applied onto the designated spot at a distance from a tip of the needle of between about 0.9 cm to about 1.1 cm.

15. The needle bending assembly of claim 14, further comprising a collar in the housing, said collar containing a rib for preventing rotational movement of the bending member at an interface.

16. The needle bending assembly of claim 11, wherein the first angle ranges from 19 degrees to about 23 degrees and the second angle ranges from 24 degrees to about 28 degrees.

17. The needle bending assembly of claim 11, wherein the dual angle bending member is an anvil having a bottom surface attached to a base, the anvil being configured for sliding from a position of the first fulcrum of the first section being in contact with the designated spot of the needle to a position of the second fulcrum of the second section being in contact with the designated spot of the needle, the sliding being in a direction perpendicular to the housing.

18. The needle bending assembly of claim 11, wherein the dual angle bending member is a wheel pivotably attached to a base, wherein the first section and the second section are positioned on an outer circumference of the wheel, the wheel being configured to rotate from a position of the first fulcrum of the first section being in contact with the designated spot of the needle to a position of the fulcrum of the second section being in contact with the designated spot of the needle.

* * * * *